(12) United States Patent
Lee et al.

(10) Patent No.: US 11,369,425 B2
(45) Date of Patent: Jun. 28, 2022

(54) LACTOFERRIN-CONJUGATED NANOPARTICLE COMPLEX AND USE THEREOF

(71) Applicant: INDUSTRY-UNIVERSITY COOPERATION FOUNDATION HANYANG UNIVERSITY, Seoul (KR)

(72) Inventors: Dong Yun Lee, Seoul (KR); Seung Jae Lee, Seoul (KR); Hyung Shik Kim, Seoul (KR)

(73) Assignee: INDUSTRY-UNIVERSITY COOPERATION FOUNDATION HANYANG UNIVERSITY, Seoul (KR)

( * ) Notice: Subject to any disclaimer, the term of this patent is extended or adjusted under 35 U.S.C. 154(b) by 0 days.

(21) Appl. No.: 17/062,497

(22) Filed: Oct. 2, 2020

(65) Prior Publication Data
US 2021/0015538 A1 Jan. 21, 2021

Related U.S. Application Data

(62) Division of application No. 15/471,905, filed on Mar. 28, 2017, now Pat. No. 10,828,083.

(30) Foreign Application Priority Data

Mar. 29, 2016 (KR) .................. 10-2016-0037860

(51) Int. Cl.
| | | |
|---|---|---|
| A61B 18/08 | (2006.01) | |
| A61K 38/06 | (2006.01) | |
| A61K 38/40 | (2006.01) | |
| A61K 41/00 | (2020.01) | |
| A61N 5/06 | (2006.01) | |
| A61K 47/69 | (2017.01) | |
| A61K 47/62 | (2017.01) | |

(52) U.S. Cl.
CPC .......... *A61B 18/082* (2013.01); *A61K 38/063* (2013.01); *A61K 38/40* (2013.01); *A61K 41/0057* (2013.01); *A61K 47/62* (2017.08); *A61K 47/6923* (2017.08); *A61K 47/6929* (2017.08); *A61N 5/062* (2013.01)

(58) Field of Classification Search
CPC .. A61B 18/082; A61K 47/6929; A61K 47/62; A61K 47/6923; A61K 38/063; A61K 38/40; A61K 41/0057; A61N 5/062
See application file for complete search history.

(56) References Cited

U.S. PATENT DOCUMENTS

| | | |
|---|---|---|
| 2008/0279946 A1 | 11/2008 | Hainfeld |
| 2011/0111002 A1 | 5/2011 | Pop |
| 2012/0052513 A1 | 3/2012 | Thalappil et al. |

FOREIGN PATENT DOCUMENTS

KR 1020100037494 4/2010

OTHER PUBLICATIONS

Cupaioli et al., "Engineered nanoparticles. How brain friendly is this new guest?" Progress in Neurobiology 119-120 (2014) 20-38 (2014).
Geldenhuys et al., "Brain-targeted delivery of doxorubicin using glutathione-coated nanoparticles for brain cancers", Pharm Dev Technol, 1-10 (2014).
Jiang et al., "Surface-functionalized nanoparticles for biosending and imaging-guided therapeutics." Nanoscaled, 2013, 5:3127-3148 (2013).
Office Action for KR 10-2017-0039228, dated May 16, 2018, 4 pages with English Abstract translation.
Program Brochure for The Polymer Society of Korea fall Meeting, Oct. 6-8, 2015, 3 pages.
Program Brochure for IUPAC-2015, 45th World Chemistry Congress, Aug. 9-14, 2015, Bexco, Busan, Korea, 3 pages.
Program Brochure for 2015 Fall Meeting of the Korean Society For Biomaterials, Sep. 17-18, 2015, Cha Bio Complex, Pangyo, Korea, 3 pages.
Program Brochure for IUMRS-ICAM, 2015, 14th International Union of Materials Research Societies—International Conference on Advanced Materials, Oct. 25-29, 2015, ICC JEJE, Korea, 3 pages.
Xie et al., "Lactoferrin-conjugated superparamagnetic iron oxide nanoparticles as a specific MRI contrast agent for detection of brain glioma in vivo", Biomaterials 32 (2011) 495-502.

*Primary Examiner* — Robert A Wax
*Assistant Examiner* — Olga V. Tcherkasskaya
(74) *Attorney, Agent, or Firm* — Adsero IP

(57) ABSTRACT

The present invention relates to a lactoferrin-conjugated nanoparticle complex and a novel use thereof. In the nanoparticle complex according to the present invention, lactoferrin or polyethylene glycol-lactoferrin is bound to metal nanoparticles, and according to this construction, it can be confirmed that the metal nanoparticles are not only efficiently targeted to the brain tumor tissues, but also the stability of the metal nanoparticles can be maintained even in the in vivo conditions, and thus it is expected in the treatment of brain tumors to be treatable to targets by approaching more fundamentally.

5 Claims, 29 Drawing Sheets

GBM region

- TUNEL Assay (AuNP with Laser)

DAPI | TUNEL | Merge

- TUNEL Assay (Lf-AuNP with Laser)

Saline | Lactoferrin | AuNP

Lf-AuNP | AuNP with Laser | Lf-AuNP with Laser

LACTOFERRIN-CONJUGATED NANOPARTICLE COMPLEX AND USE THEREOF

TECHNICAL FIELD

The present invention relates to a lactoferrin-conjugated nanoparticle complex and a use thereof.

BACKGROUND ART

The aging rate in Korea is the fastest around the world, and demand for therapeutic agents of degenerative brain diseases and senile diseases geriatric diseases related to this is increasing rapidly. Particularly, the top cause of death among people over 65 years of age is cancers, which are a cause of death of 865.4 persons of deaths per 100,000 people, followed by cerebrovascular disease (410.7 persons), heart disease (332.6 persons) and diabetes (146.6 persons). In particular, according to the Central Cancer Registry data released in 2013, brain tumors that refer to all the tumors within the skull were 1,679 cases per year for men and women together, where by age group, the age of 50s was the highest at 17.6%, followed by 60s at 16.5% and 70s at 14.9%, showing high incidence rate in the elderly. There are concerns that frequent administration of low half-life intravenous infusions to older patients does not only cause stress to the patients, but also does not provide effective therapeutic effects. Therefore, it is urgent to develop an orally absorptive therapeutic agent for brain tumors which can provide convenience to patients through oral administration with a long half-life and prevent stress induced by drug administration.

On the other hand, the treatment of brain tumors may include three largely, where the first is surgical surgery, second radiation therapy, and third anticancer chemotherapy, and the like. Currently, drugs such as avastin, temozolomide and doxorubicin, which are anticancer drugs, have been widely used in the treatment of brain tumor, but it has been known that these drugs have severe side effects such as nausea and vomiting, stomatitis, diarrhea, abdominal pain, hair loss and infection (pneumonia, urinary tract infection). As other therapies, gene therapy, immunotherapy, photothermal or photodynamic therapy, and the like have been studied, and recently, studies have been continued in the direction of reducing side effects of the anticancer drugs through target therapy of brain tumors after synthesizing target antibodies against intracellular/extracellular specific substances of brain tumors to nanoparticles for malignant brain tumor treatment. Among various nanoparticles, gold nanoparticles capable of generating heat through surface plasmon resonance at the near-infrared wavelength have been mainly used, and various photosensitizers have been used together to generate a sufficient amount of heat for killing cancer cells. However, even in the treatment with gold nanoparticles, there is a disadvantage that the oral absorption rate is very low due to the low pH in the gastrointestinal tract, which is a limitation in the use as a therapeutic agent.

Under these circumstances, as a part of target treatment to brain tumors, studies on nanoparticles having improved in vivo stability and brain tissue targeting effect have been actively conducted (Korean Laid-open Patent Publication No. 10-2010-0037494), but it is still an incomplete state.

DISCLOSURE

Technical Problem

The present invention has been conceived to solve the problems as described above, and the inventors have confirmed that by conjugating lactoferrin or polyethylene glycol-lactoferrin to glutathione-conjugated or coated gold nanoparticles, the gold nanoparticles are not only effectively targeted to brain tumor tissues, but also stability of the metal nanoparticles can be maintained even under conditions such as strong acidity, and have completed the present invention on the basis thereof.

Accordingly, it is an object of the present invention to provide a nanoparticle complex with improved brain tumor targeting and bioavailability.

In addition, it is another object of the present invention to provide a novel use of the nanoparticle complex for treating brain tumors.

However, the technical problems to be achieved by the present invention are not limited to the above-mentioned problems, and other problems not mentioned can be clearly understood by those skilled in the art from the following description.

Technical Solution

In order to accomplish the object of the present invention, the present invention provides a nanoparticle complex comprising metal nanoparticles, glutathione, and lactoferrin.

In one embodiment of the present invention, the metal nanoparticles may be selected from the group consisting of gold nanoparticles, iron oxide nanoparticles, and silver nanoparticles.

In another embodiment of the present invention, the nanoparticle complex may comprise metal nanoparticles surface-modified with lactoferrin and glutathione, and the lactoferrin may be surface-modified with a biocompatible polymer.

In another embodiment of the present invention, the biocompatible polymer may be selected from the group consisting of polyethylene glycol, polycaprolactone, polylactic acid, polyglycolic acid, polylactate-co-glycolic acid, poly(3-hydroxybutyrate-co-3-hydroxyvalerate) (PHBV), poly(L-lactide-co-caprolactone, and poly(L-lactide-co-D-lactide), and the biocompatible polymer may be modified to have a thiol (—SH) group at one terminal thereof.

In another embodiment of the present invention, the lactoferrin and the glutathione may be bound to the metal nanoparticles by disulfide bonds.

In another embodiment of the present invention, the nanoparticle complex may have an average diameter of 4 nm to 20 nm.

In addition, the present invention provides a pharmaceutical composition for treating brain tumors, comprising the nanoparticle complex, and provides a composition for a photothermal or photodynamic therapy comprising the nanoparticle complex.

In one embodiment of the invention, the pharmaceutical composition may further comprise a pharmaceutically acceptable carrier.

In another embodiment of the invention, the composition may be for oral administration.

In another embodiment of the present invention, the composition may be targeted to brain tissues.

In addition, the present invention provides a treatment method of brain tumors and a photothermal or photodynamic treatment method, comprising a step of administering the nanoparticle complex to a subject.

The present invention also provides a therapeutic use of the nanoparticle complex for brain tumors.

Effects of the Invention

In the nanoparticle complex according to the present invention, lactoferrin or polyethylene glycol-lactoferrin is bound to metal nanoparticles, and according to this construction, it can be confirmed that the metal nanoparticles are not only efficiently targeted to the brain tumor tissues, but also the stability of the metal nanoparticles can be maintained even in the in vivo conditions, and thus it is expected in the treatment of brain tumors to be treatable to targets by approaching more fundamentally.

DETAILED DESCRIPTION FOR CARRYING OUT THE INVENTION

Figure 1:
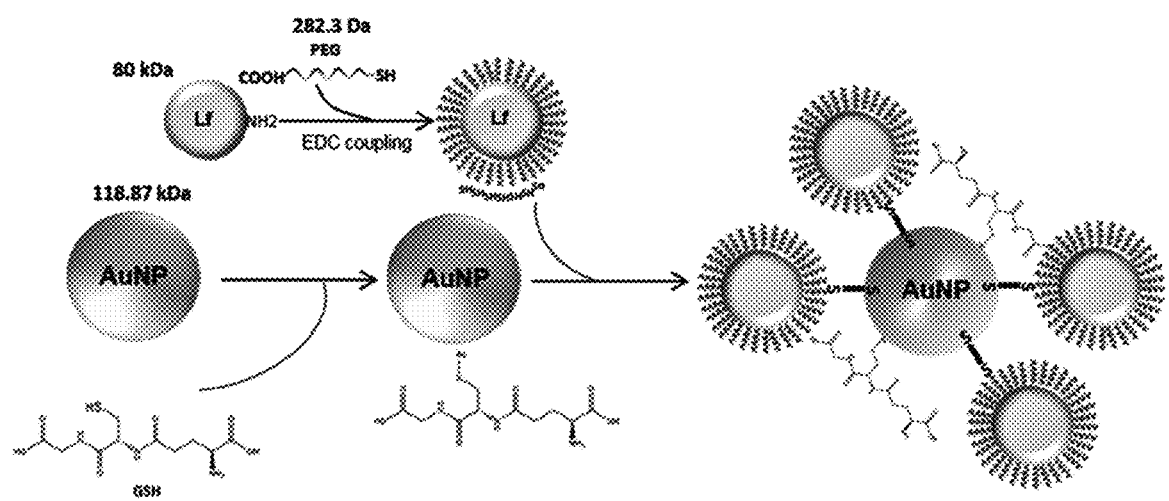
FIG. 1 is a diagram schematically showing a process for producing a gold nanoparticle complex.

Hereinafter, the present invention will be described in detail.

The present invention provides a nanoparticle complex comprising metal nanoparticles, glutathione, and lactoferrin.

In the present invention, the metal nanoparticles have a construction generating heat by surface plasmon resonance upon electromagnetic wave irradiation, which serve to form a central part of the nanoparticle complex. The metal nanoparticles may be preferably gold nanoparticles, iron oxide nanoparticles, or silver nanoparticles, and most preferably gold nanoparticles, but are not limited thereto. In addition, non-metallic nanoparticles, such as silica nanoparticles, may be also substituted to be applied, if necessary.

Although there was a difficulty in using conventional metal nanoparticles as a therapeutic agent because of their low oral absorption rate due to a low pH in the gastrointestinal tract, glutathione may be bound thereto or coated thereon, so that the biocompatibility of the metal nanoparticles may be improved and the stability may be maintained even at low pH, and specifically the glutathione forms a disulfide bond with the surface of the metal nanoparticle. In addition, the metal component of the nanoparticles is not particularly limited as long as it is a metal capable of generating heat by irradiation of an electromagnetic wave. In one embodiment, the metal component may be a gold (Au) component having absorbance in the near infrared region.

Lactoferrin used in the present invention binds to iron in the human body to turn into a powerful antioxidant, and is a substance exhibiting activity such as inhibition of bacterial growth in the body, which is known to have a high content in a breast fluid, and in particular, to be contained the highest in colostrums.

Particularly, lactoferrin is a ligand capable of binding to LRP (low-density lipoprotein receptor related protein), which is one of cell membrane proteins, and a large number of lactoferrin receptors are known to be expressed in the small intestine epithelium. Thus, in the present invention, lactoferrin was used as a construction for enhancing targeting of brain tumors and bioavailability of metal nanoparticles, particularly oral absorption rate. The lactoferrin may be bound to or coated on the surface of the metal nanoparticles, and specifically, the lactoferrin forms a disulfide bond with the metal nanoparticle surface.

The nanoparticle complex of the present invention may further comprise a biocompatible polymer in order to minimize modification of lactoferrin. Specifically, by modifying the lactoferrin surface with the biocompatible polymer, the deformation of the lactoferrin can be minimized in the gastrointestinal tract and blood circulation. Through such a construction, the oral absorption rate of the nanoparticle complex is improved and, ultimately, target characteristics into brain tissues are increased. Moreover, a certain distance between the nanoparticle complexes is maintained by repulsion between lactoferrin and the bound biocompatible polymer to prevent an aggregation phenomenon between nanoparticles, thereby ultimately contributing to enhance photothermal or photodynamic therapeutic effects.

The biocompatible polymer may be preferably a monomer or a polymer of a polysaccharide having a bio-friendly feature, and preferably, the polymer may be polyethylene glycol, polycaprolactone, polylactic acid, polyglycolic acid, polylactate-co-glycolic acid, poly(3-hydroxybutyrate-co-3-hydroxyvalerate) (PHBV), poly(L-lactide-co-caprolactone) and poly(L-lactide-co-D-lactide), and most preferably, polyethylene glycol, and if necessary, the biocompatible polymer may be modified to have a thiol (—SH) group at one terminal thereof, but is not limited thereto.

The nanoparticle complex of the present invention may preferably have an average diameter of 4 nm to 20 nm. The therapeutic effect may be insignificant, if the diameter of the nanoparticles is too small beyond the above range, whereas a problem that a transmission rate of the blood brain barrier (BBB) is decreased may be caused, if the diameter of the nanoparticles is too large.

In the nanoparticle complex of the present invention, the binding ratio of lactoferrin to polyethylene glycol may be 1:100 to 1:25, and most preferably 1:50, but is not limited thereto. In addition, the binding ratio of the lactoferrin to which polyethylene glycol is bound and the gold nanoparticles to which glutathione is bound may be 10:1 to 3:1, and most preferably 4.5:1, but is not also limited thereto.

Meanwhile, for the purpose of the present invention, in terms of uses, the nanoparticle complex can be used for brain tumor treatment, photothermal treatment and photodynamic treatment, and in terms of administration methods, it can be used for oral administration, since it exhibits high stability in the gastrointestinal tract.

In one example of the present invention, the gold nanoparticle complex of the present invention was prepared by reacting glutathione-bound gold nanoparticles with polyethylene glycol-bound lactoferrin, and it could be confirmed that in the gold nanoparticle complex, physical features of nanoparticles themselves, that is, significant absorption peaks for near infrared wavelength bands and exothermic effects were maintained. Furthermore, in another example of the present invention, it could be confirmed that stability was maintained even under strongly acidic conditions, cytotoxicity to small intestinal endothelial cells and vascular endothelial cells was low, and oral absorption rate enhancement effect was excellent. Besides, it could be confirmed that the brain tissue targeting effect was excellent in the brain tumor animal model, and it could be seen to be used for the treatment of brain tumors.

Accordingly, the present invention provides a pharmaceutical composition for treating brain tumors, comprising the nanoparticle complex as an effective ingredient; a use of the nanoparticle complex for treating brain tumors; and a method for treating brain tumors comprising a step of administering to a subject a therapeutically effective amount of the nanoparticle complex.

As used herein, the term "treatment" means all the actions in which symptoms of brain tumors are improved or mitigated by the administration of the pharmaceutical composition according to the present invention.

In the present invention, "subject" means a subject in need of treatment for brain tumors, and more specifically a mammal such as a human or nonhuman primate, a mouse, a dog, a cat, a horse and a cow.

The term "tumor," which is a target disease to be treated in the present invention, refers to a group of diseases characterized in that cells can over-proliferate and infiltrate into surrounding tissues when normal cell death balance is broken, and considering the brain tissue targeting effect of the nanoparticle complex, preferably, the tumor may be brain cancer (brain tumor), and more specifically, Glioblastoma multiforme (GBM), without being limited thereto.

The pharmaceutical composition of the present invention may comprise, in addition to the effective ingredient, a pharmaceutically acceptable carrier. Here, the pharmaceutically acceptable carrier is one typically used upon formulation, and includes lactose, dextrose, sucrose, sorbitol, mannitol, starch, acacia, rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate and mineral oil, and the like, but is not limited thereto. In addition to the above ingredients, a lubricant, a wetting agent, a sweetener, a flavoring agent, an emulsifier, a suspending agent, a preservative, and the like may be further included.

The pharmaceutical composition of the present invention can be administered orally or parenterally (for example, intravenously, subcutaneously, intraperitoneally or topically), most preferably orally, depending on the intended method. The dosage varies depending on patients' conditions and weights, degrees of disease, drug forms, administration routes and times, but can be appropriately selected by those skilled in the art.

The pharmaceutical composition of the present invention is administered in a pharmaceutically effective amount. In the present invention, "pharmaceutically effective amount" means an amount sufficient to treat a disease at a reasonable benefit/risk ratio capable of being applied to medical treatment, and an effective dosage level may be determined depending on types of patient's diseases, severity, activity of drugs, sensitivity to drugs, administration times, administration routes and release rates, treatment duration, factors including co-administered drugs, and other factors well known in the medical field. The pharmaceutical composition according to the present invention can be administered as an individual therapeutic agent or in combination with other therapeutic agents, sequentially or simultaneously with conventional therapeutic agents, and singly or multiply. It is important to administer the amount in which the maximum effect can be obtained in a minimal amount without side effects in consideration of all the factors, which can be easily determined by those skilled in the art.

The present invention also provides a composition for photothermal/photodynamic therapy comprising the nanoparticle complex as an effective ingredient; a use of the nanoparticle complex for photothermal/photodynamic therapy; and a photothermal/photodynamic treatment method comprising a step of administering to a subject a therapeutically effective amount of the nanoparticle complex.

The composition of the present invention can be used as a composition for photothermal therapy using the property of metal nanoparticles that generate heat by electromagnetic wave irradiation. The photothermal therapy means a way in which light energy is converted into heat energy when a ray (light) of a wavelength is shot, and the heat energy from the light burns and treats cancer cells. Laser irradiation generates heat by the surface plasmon resonance (SPR) phenomenon and radiates it around to affect an external region (for example, tumor cells). As one example, cancer cells can be killed.

The composition of the present invention can also be used as a composition for photodynamic therapy, using a photosensitizer and a light beam. The photodynamic therapy means a treatment method comprising processes of treating a subject in a pathological state with a photosensitizer and irradiating the subject with a light beam to obtain a therapeutic effect by activating the photosensitizer. The "photosensitizer" comprehensively means a compound capable of releasing a biological intermediate substance (for example, a radical or a cytotoxic material) that can absorb light energy when exposed to a light source of an appropriate wavelength and then damage or break down target cells by photochemical reactions. When administered to a living body, the photosensitizer exhibits selective toxicity to cancer cells by specifically binding to certain target cells (for example, cancer cells), and then being activated by a light source to generate a toxic substance capable of killing cancer cells. An example of compounds that can be used as such a photosensitizer includes chlorin compounds, bacterioclorin compounds, phthalocyanine compounds, porphyrin compounds, purine compounds, merocyanine compounds, psoralen compounds, benzoporphyrin derivative compounds, and delta-aminolevulinic acid capable of generating a photosensitizer such as porfimer sodium and protoporphyrin IX, indocyanine green (ICG), methylene blue, toluidine blue, texaphyrin compounds, and the like.

In the present invention, the energy amount of the light beam for generating heat energy or activating the photosensitizer is suitably selected and used depending on use environments and purposes. For example, appropriate wavelengths, powers, power densities, energy densities, and application periods proportional to the treating time by the photosensitizer, and the like are appropriately selected and adjusted. As the wavelength of the light beam, any wavelength that can be absorbed by the metal nanoparticles or the photosensitizer can be also used, and any wavelength, which can cause the desired biological response to the target cells, can be included without limitation.

In the present invention, as the light source generating light beams, any light source that generates a wavelength capable of generating heat energy by supplying necessary light energy or activating a photosensitizer, can be also used. A specific example of the light source may include a laser, a lamp, an optoelectric magnetic device, a diode, or a diode-laser, and the like.

Hereinafter, preferred examples will be described in order to facilitate understanding of the present invention. However, the following examples are provided only for easier understanding of the present invention, and the contents of the present invention are not limited by the following examples.

PREPARATION EXAMPLE

Preparation Example 1: Preparation of Lactoferrin-Conjugated Gold Nanoparticle Complex After dissolving $HAuCl_4$ (1 mM), glutathione (37.8 mM), and NaOH (178 mM) in 55.6% (v/v) aqueous methanol solution (methanol (115 ml) and distilled water (303 ml)), $NaBH_4$ was added thereto to reduce gold ions ($Au^{3+}$), and the solution was stirred at 100° C. for 48 hours. NaCl (68 mM) was added to the mixed solution, and then glutathione-coated gold nanoparticles (GSH-AuNP) were precipitated by centrifugation at 3200 RCF. Thereafter, methanol was vaporized at room temperature for 24 hours to prepare a lactoferrin-conjugated gold nanoparticle complex.

Preparation Example 2: Preparation of Polyethylene Glycol-Lactoferrin-Conjugated Gold Nanoparticle Complex

2-1. Preparation of Polyethylene Glycol-Bound Lactoferrin

After dissolving polyethylene glycol (SH-PEG-COOH, 3.5 µg) in PBS buffer (2 ml), EDC (47.75 mg) and NHS (57.55 mg) were dissolved again therein, and the solution was stirred for 15 minutes. After 15 minutes, lactoferrin (10 mg) was dissolved and again stirred at 4° C. for 24 hours. Thereafter, after dialysis at 4° C. for 24 hours using a 10 kDa membrane, the resulting product was lyophilized to prepare polyethylene glycol-bound lactoferrin (SH-PEG-Lactoferrin).

2-2. Preparation of Polyethylene Glycol-Lactoferrin-Conjugated Gold Nanoparticle Complex A lactoferrin-PEG mixture in which the polyethylene glycol-bound lactoferrin (SH-PEG-Lactoferrin) prepared in Preparation Example 2-1 above and polyethylene glycol (SH-PEG-COOH) were mixed in a ratio of 1:4, was dissolved in PBS (2 ml) at a concentration of 1 mM, this solution was again mixed with a solution of gold nanoparticles, in which glutathione-coated gold nanoparticles (GSH-AuNP) were dissolved in PBS at a concentration of 20 µM, to prepare 4 ml of a mixed solution, and then stirred at 4° C. for 24 hours. Thereafter, after dialysis at 4° C. for 24 hours using a 100 kDa pore membrane, the resulting product was lyophilized to prepare a polyethylene glycol-lactoferrin-conjugated gold nanoparticle complex. The process for preparing the polyethylene glycol-lactoferrin-conjugated gold nanoparticle complex was schematically shown in FIG. 1, and in the following examples, this was referred to as a 'gold nanoparticle complex.'

EXAMPLE

Example 1: Process for Preparing Gold Nanoparticle Complex and Identification of its Physical Properties This example was intended to specifically identify products by each step from the processes for preparing the gold nanoparticle complexes according to Preparation Examples 1 and 2 above and to identify specific physical features of the gold nanoparticle complexes.

1-1. Identification of Products from Preparing Processes

The glutathione-coated gold nanoparticles according to Preparation Example 1 and the polyethylene glycol-bound lactoferrin according to Preparation Example 2-1 were identified through H-NMR and SDS-PAGE and BCA assay, and the gold nanoparticle complex according to Preparation Example 2-2 was observed using BCA assay and HR-TEM (high resolution-transmission electron microscopy).

Figure 2A:
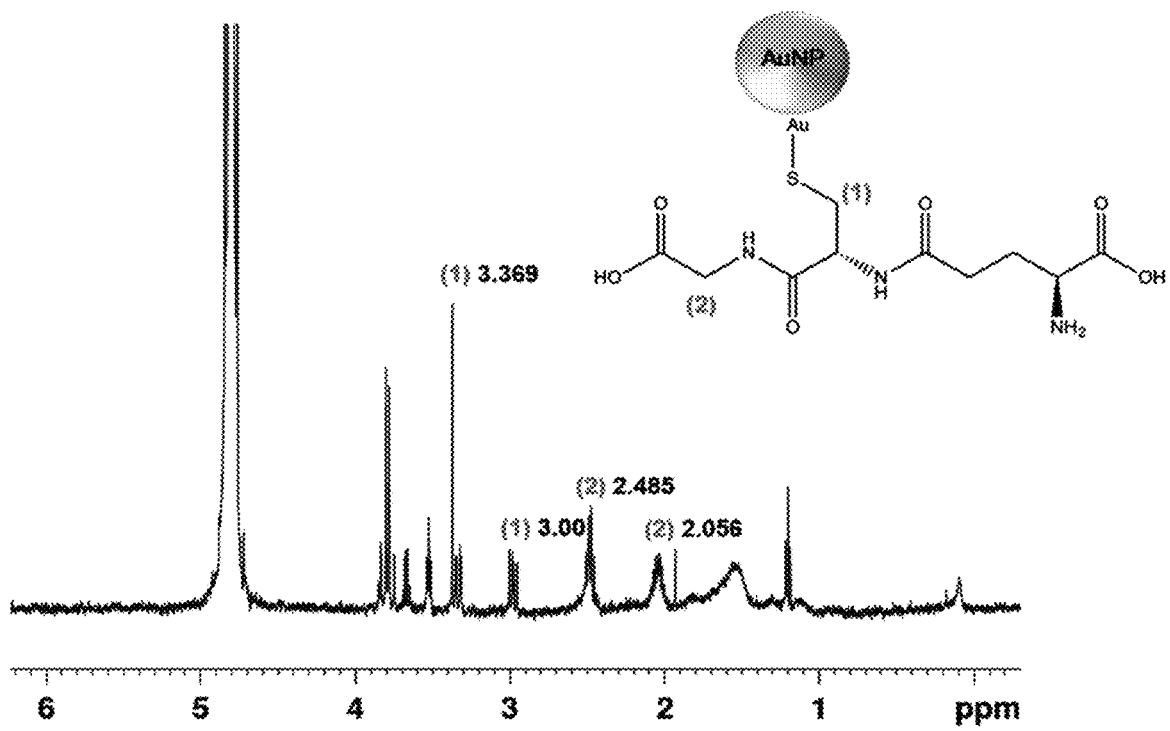
FIG. 2a is the result of confirming glutathione-coated gold nanoparticles through H-NMR.
Figure 2B:
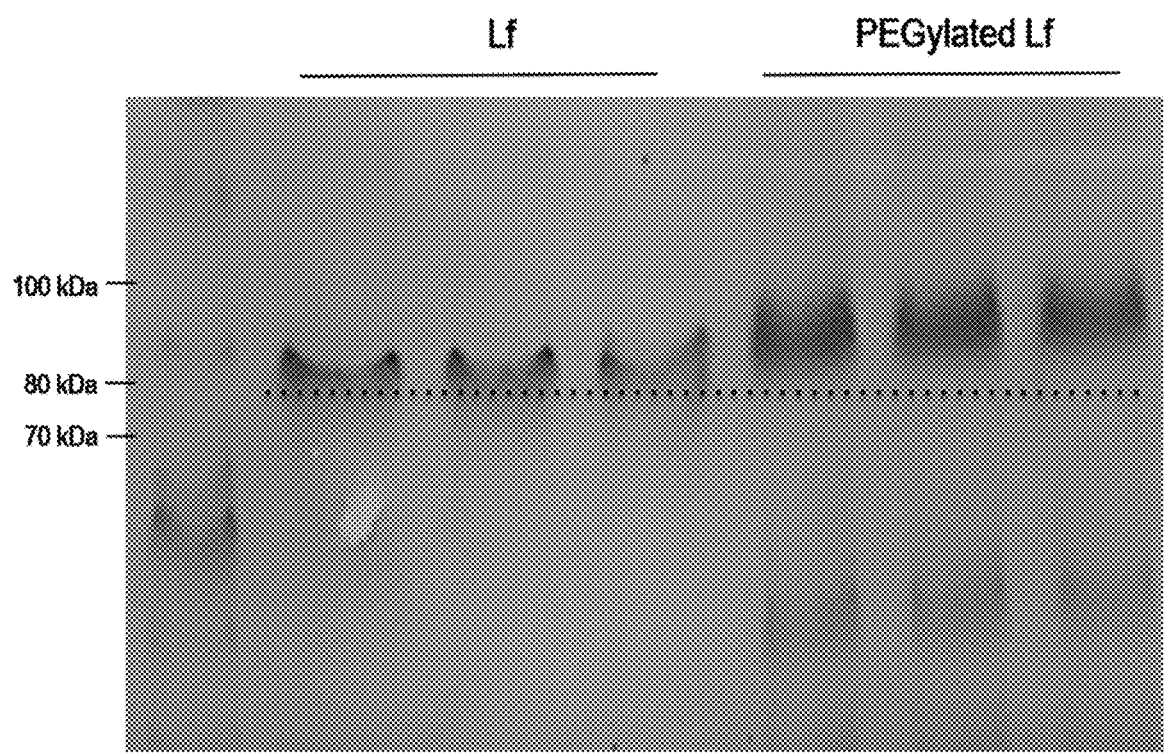
FIG. 2b is the result of confirming polyethlylene glycol-bound lactoferrin (Lf-PEG) through SDS-PAGE.

As a result, as shown in FIGS. 2a and 2b, it could be confirmed by observing peaks of 3.369 ppm, 2.485 ppm, and 2.056 ppm in H-NMR that glutathione was bound to the surface of the gold nanoparticles, and the band of lactoferrin (Lf) itself was detected at about 80 kDa, while the band of the polyethylene glycol-bound lactoferrin (Lf-PEG) was formed above the Lf band, whereby it could be confirmed to synthesize Lf-PEG.

Figure 2C:
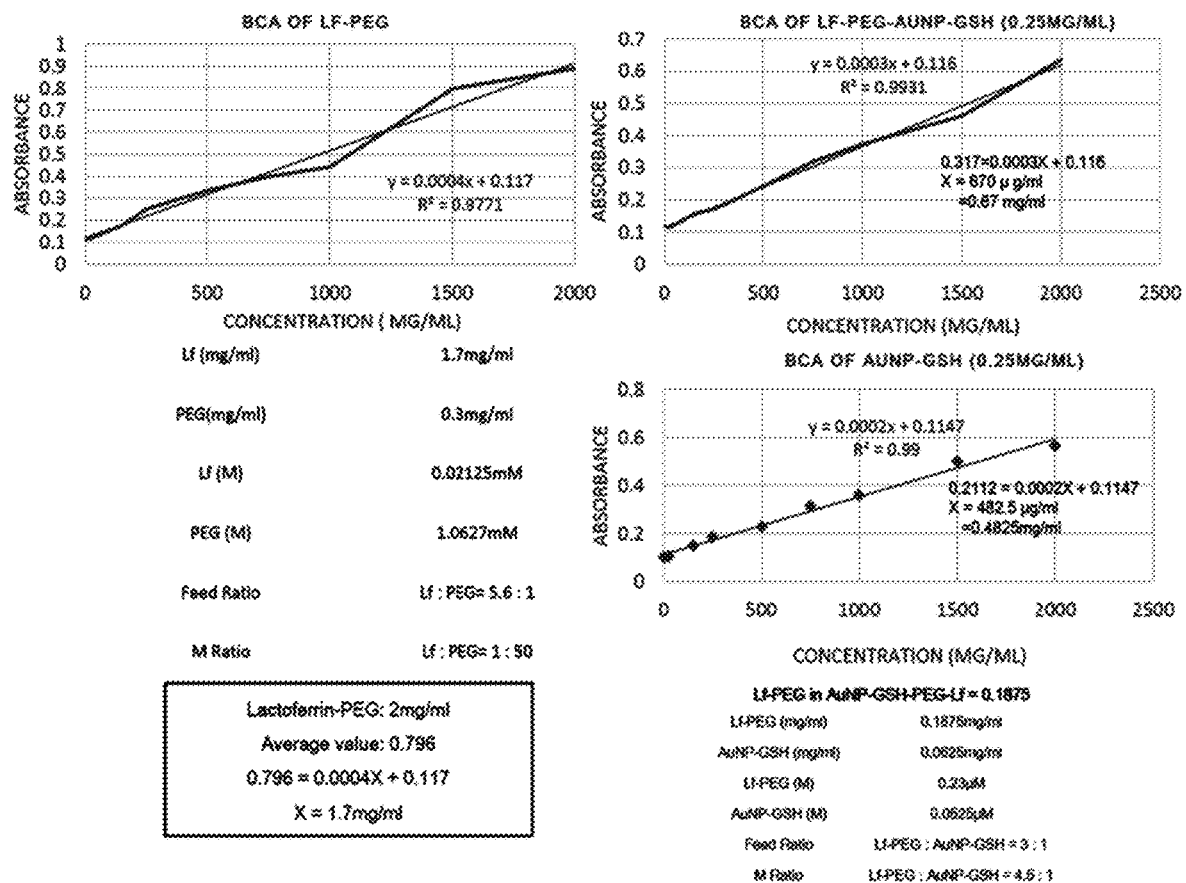
FIG. 2c is the results of confirming the binding ratio between lactoferrin and polyethylene glycol and the binding ratio between polyethylene glycol-bound lactoferrin (Lf-PEG) and glutathione-coated gold nanoparticles through a BCA protein assay kit.

On the other hand, as shown in FIG. 2c, when the molar concentration (M) ratio of polyethylene glycol-bound lactoferrin (SH-PEG-Lactoferrin) was identified by the BCA assay as a protein quantification technique, it could be seen that the binding ratio of lactoferrin (Lf) and polyethylene glycol was 1:50 (see FIG. 2c). In addition, when the BCA assay was equally performed for the gold nanoparticle complex formed by the binding between the gold nanoparticles and the Lf-PEG, it could be seen that the binding ratio of polyethylene glycol-bound lactoferrin (Lf-PEG) and glutathione-conjugated gold nanoparticles was 4.5:1 (see FIG. 2c).

Figure 3:
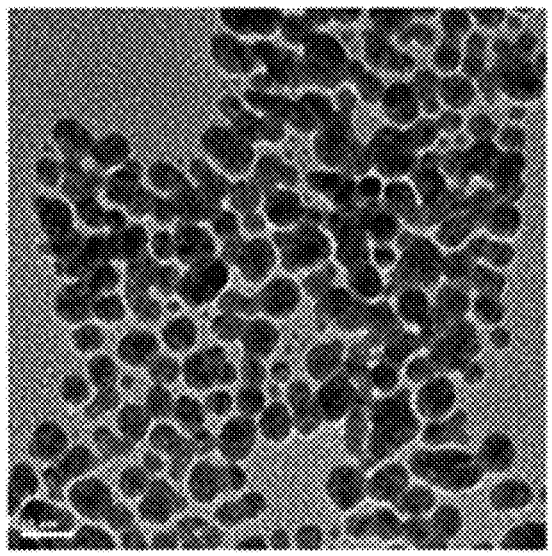
FIG. 3 is the results of observing general gold nanoparticles (left side) and gold nanoparticle complexes (right side) with a transmission microscope.
Figure 3:
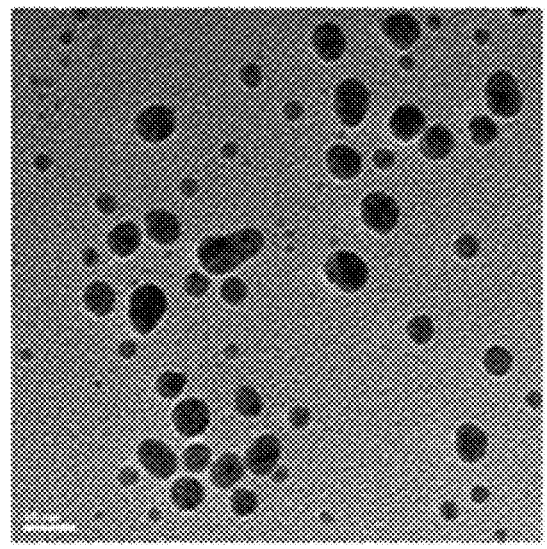

Finally, when observed by a transmission microscope, it could be confirmed that the size of general gold nanoparticles (AuNP) was 4.56 nm on average and the size of gold nanoparticle complex (Lf-AuNP) of the present invention was 5.02 nm on average, and in the case of AuNP the gold nanoparticles were aggregated to each other, while in the case of Lf-AuNP the gold nanoparticles aggregated by PEG were released (see FIG. 3).

1-2. Identification of Physical Properties of Gold Nanoparticle Complex

Figure 4:
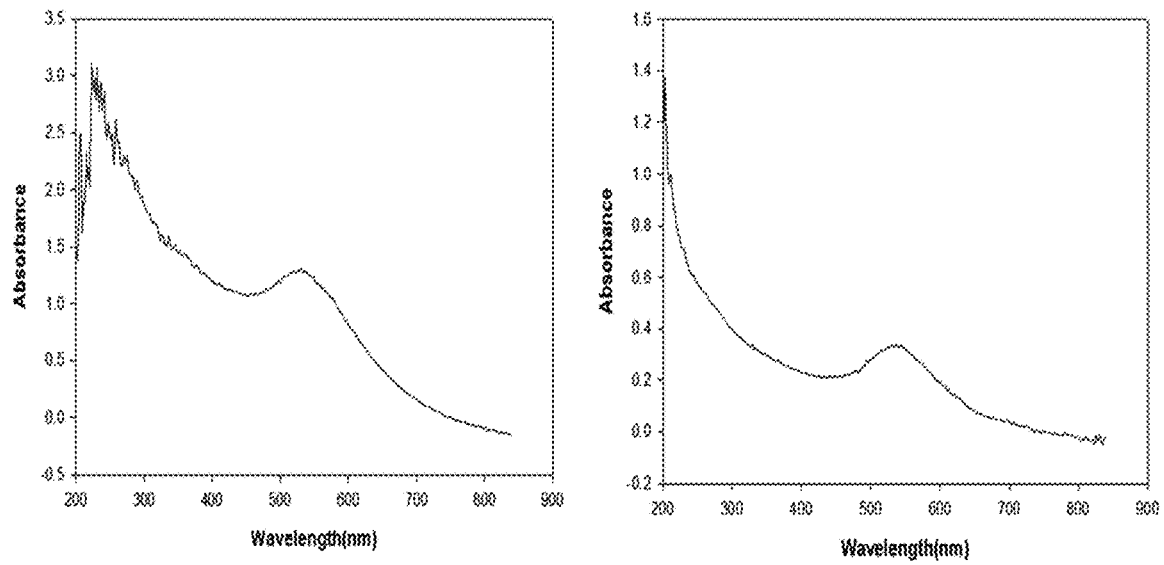
FIG. 4 is the result of measuring absorbance after irradiating general gold nanoparticles (left side) and gold nanoparticle complexes (right side) with light of near-infrared wavelength bands.

In order to confirm whether the gold nanoparticles retain their original properties despite the formation of the gold nanoparticle complex, the absorbance values at the respective wavelengths were measured using a UV-vis spectrophotometer, and the exothermic effect by the light at the near-infrared (NIR) wavelength bands was identified (see FIG. 4). Specifically, general gold nanoparticles and the gold nanoparticle complex were prepared by 8 mg/ml, and a laser having a wavelength of 532 nm was irradiated thereto under a condition of 4 w/cm$^2$ for 240 seconds using an LRS-0532 DPSS Laser System Laser Glow Part Number: R5310B1FL. Thereafter, the temperatures of each time zone were measured using an FLIR C2 thermal imaging camera at every 0, 3, 10, 30, 60, 120, 180, 240, 300, 330, and 400 seconds to compare the exothermic effects.

Figure 5A:
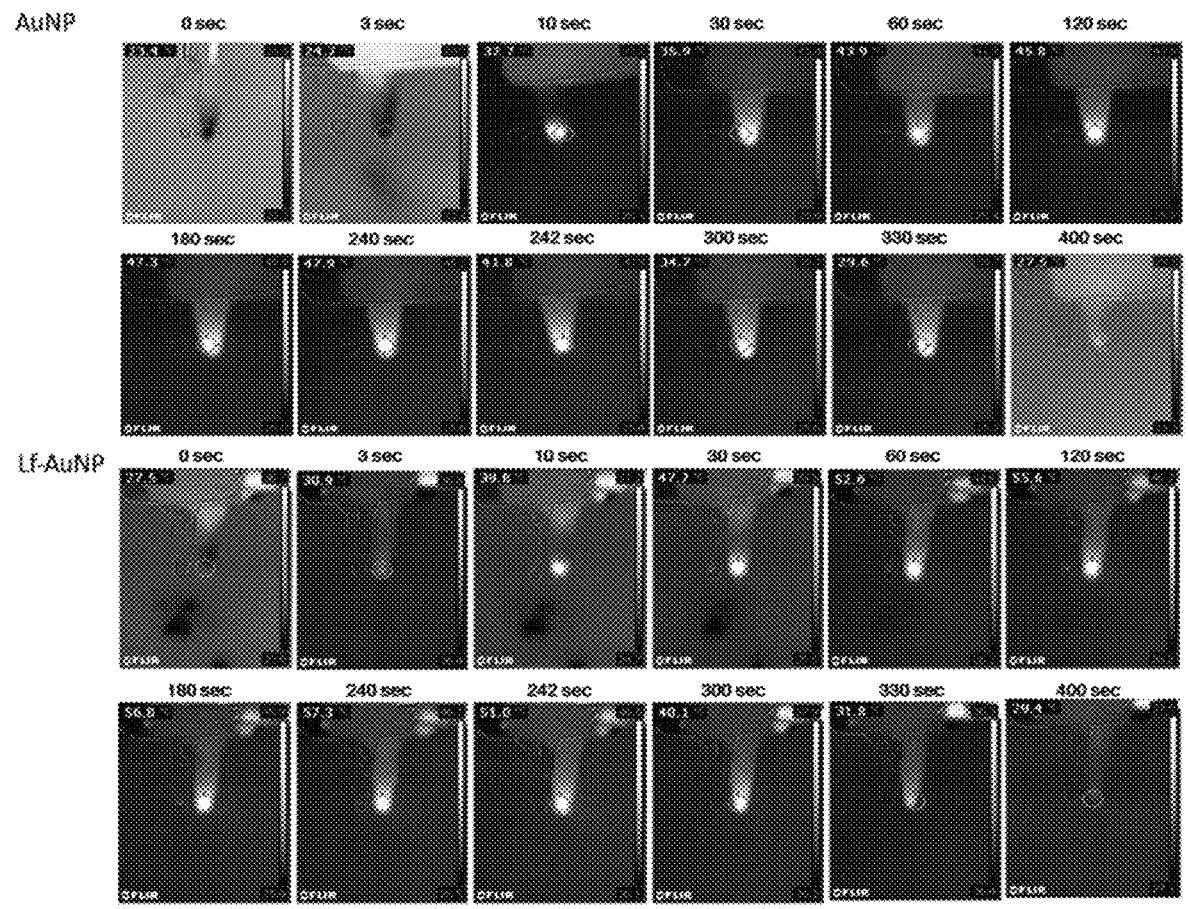
FIG. 5a is the result obtained by irradiating a gold nanoparticle complex (Lf-AuNP; lower side) with light having a wavelength of 532 nm and then comparing the temperature change according to this with a group treated with general gold nanoparticles (AuNP; lower side).
Figure 5B:
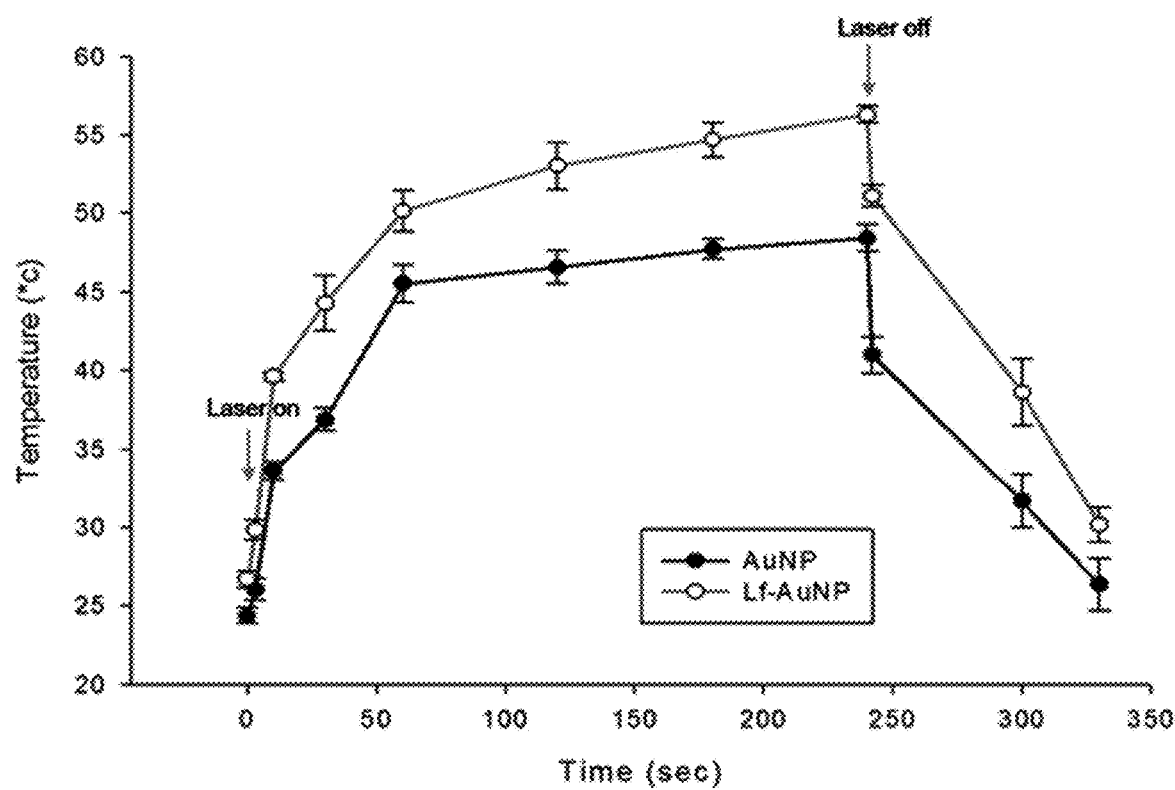
FIG. 5b is the result quantitatively showing the temperature change of gold nanoparticle complexes (Lf-AuNP) and general gold nanoparticles (AuNP) over time after irradiation them with light having a wavelength of 532 nm.

As a result, as shown in FIG. 5, in the case of the gold nanoparticle complex of the present invention, the excellent exothermic effect on light with a wavelength of 532 nm was confirmed, like general gold nanoparticles (AuNP), and thus it could be confirmed that even if Lf-PEG is conjugated, the properties of the gold nanoparticles are maintained. Besides, by maintaining the distance of about 5 nm between the gold nanoparticles due to the action of the repulsion by the Lf-PEG bond, a better exothermic effect could be observed over general gold nanoparticles with frequent aggregation phenomenon. Actually, as shown in FIG. 5b, it could be confirmed that in the case of general gold nanoparticles, heat was generated up to 47.9° C., whereas in the gold nanoparticle complex of the present invention, heat was generated up to 57.3° C.

Example 2: Identification of Stability of Gold Nanoparticle Complex Under Strongly Acidic Conditions In order to confirm whether the gold nanoparticle complex can maintain stability in the gastrointestinal tract under strongly acidic conditions, this example measured absorbance values at a wavelength of 532 nm, which were confirmed in Example 1-2 above, at pH 5 and pH 2, which are acidity in intestines and stomach. Specifically, the gold nanoparticle complex was exposed to a condition of pH 2 for 0, 1, 2, 6 and 12 hours and to a condition of pH 5 for 0, 1, 2, 6 and 12 hours, and the gold nanoparticle complex was exposed to a condition of pH 2 for 2 hours and then to the changed pH 5 for 0, 1, 4 and 7 hours, as a condition for simulating the environment passing the stomach and entering into the intestines. Then, for each gold nanoparticle complex, the absorbance values at a wavelength of 532 nm were measured using a spectrophotometer.

Figure 6A:
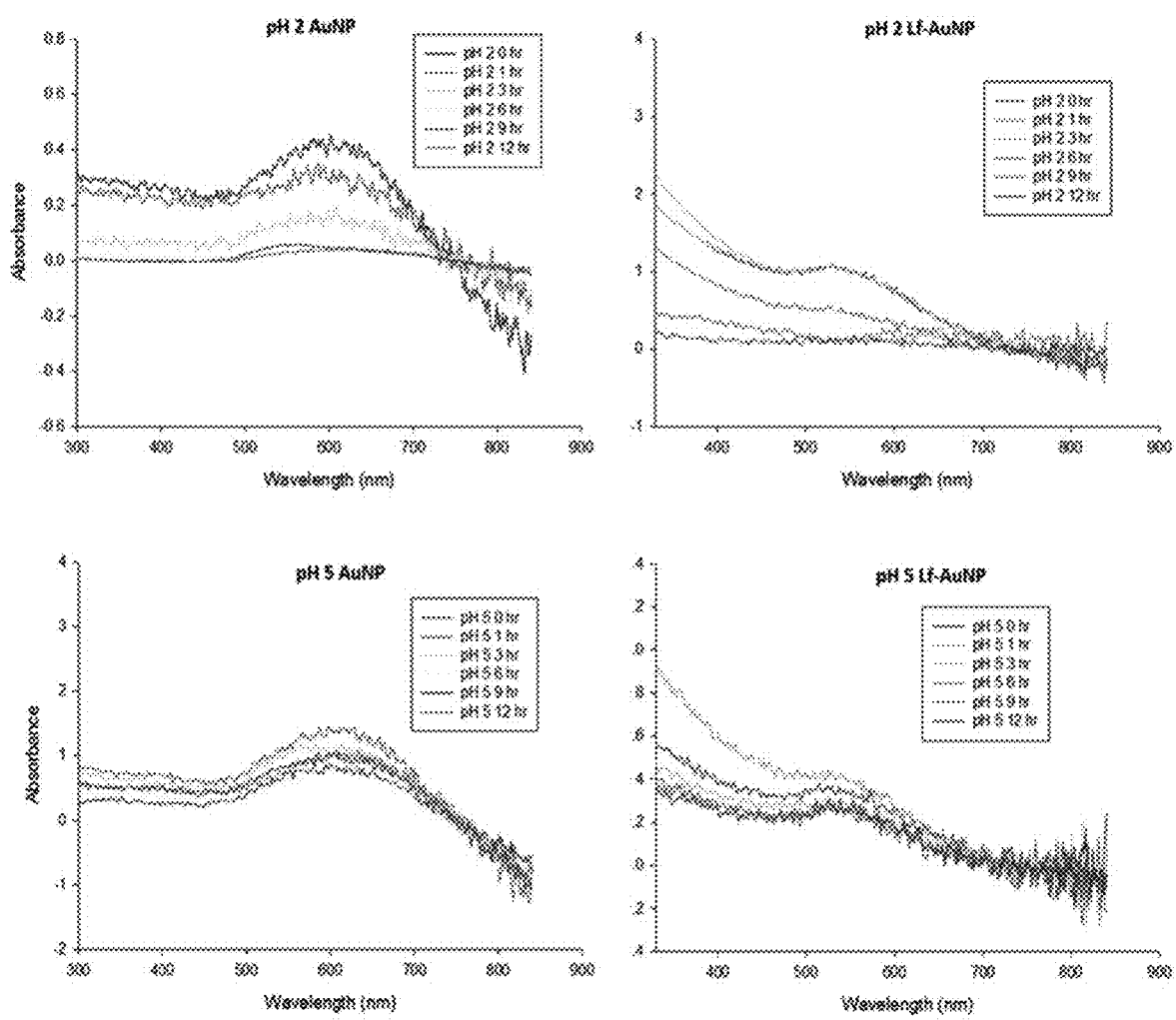
FIG. 6a is the result of measuring absorbance by wavelength of general gold nanoparticles (AuNP) and gold nanoparticle complexes (Lf-AuNP) over time under the condition of pH 2 or 5 of the stomach and intestine where the drug is exposed upon oral administration.
Figure 6B:
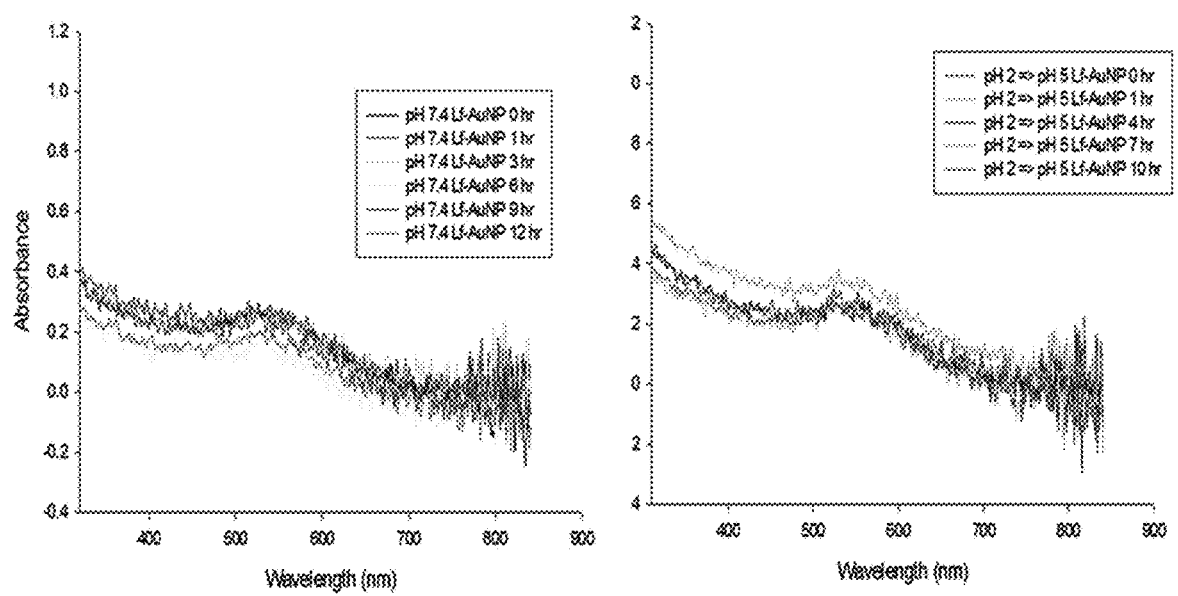
FIG. 6b is the results of measuring absorbance by wavelength of gold nanoparticle complexes (Lf-AuNP) over time under the condition of pH 7.4, or changing from pH 2 to pH 5 where the drug is exposed upon oral administration.

As a result of measuring the absorbance values under a strongly acidic condition (pH 2 or pH 5), as shown in FIG. 6a, it could be confirmed that the gold nanoparticle complex (Lf-AuNP) increases absorbance at a wavelength of 532 nm as in gold nanoparticles (AuNP). In addition, when the pH was changed from a condition of pH 2 to a condition of pH 5, the increase in absorbance of the gold nanoparticle complex was similar to that of neutral (pH 7.4), as shown in FIG. 6b, and thus it could be seen that the stability of the gold nanoparticle complex can be maintained in an in vivo condition, particularly, the gastrointestinal tract.

Example 3: Identification of Stability of Gold Nanoparticle Complex to Protease

In this example, a pepsin hydrolysis assay was performed to demonstrate the stability (inhibitory effect of lactoferrin degradation) of the gold nanoparticle complex against pepsin, which is a protease secreted from stomach. The lactoferrin (Lf) and the gold nanoparticle complex (Lf-AuNP) were exposed to pepsin for 0, 10, 20, 30, 60, 120 and 240 minutes, respectively, and then electrophoresis was performed, where the lactoferrin (Lf) was set to the same amount as that of lactoferrin bound to the gold nanoparticle complex. Specifically, while the lactoferrin and gold nanoparticle complex were dissolved in 10 mM HCl at 1 mg/ml, 40 ng/ml of pepsin was added thereto at a ratio of 1:1. Thereafter, after reacting the solution for 0, 10, 20, 30, 60, 120 and 240 minutes, the reactant was reacted with an SDS sample solution at a ratio of 1:1 to perform electrophoresis.

Figure 7A:
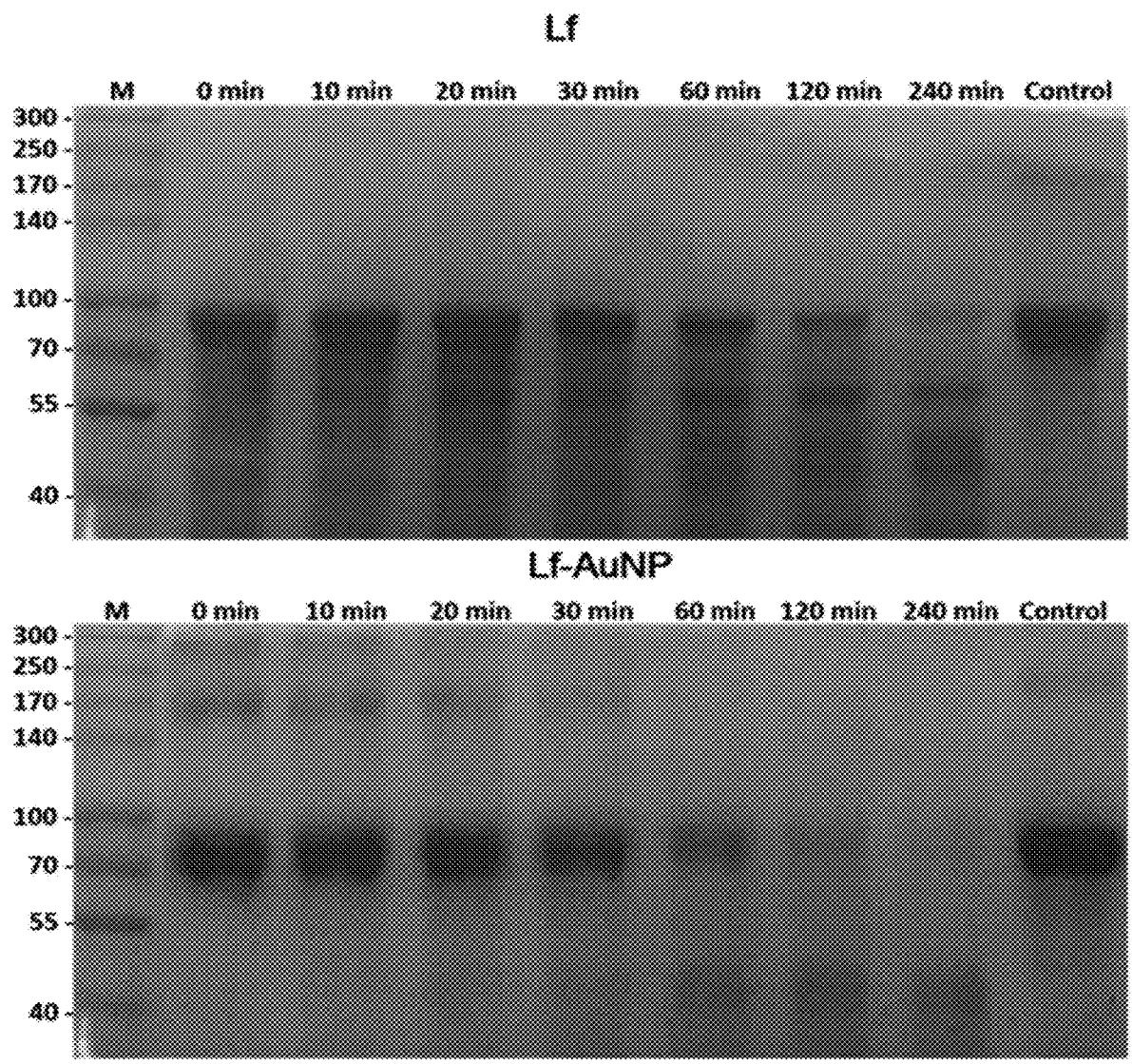
FIG. 7a is the result of performing Pepsin Hydrolysis assay to demonstrate stability of gold nanoparticle complexes (Lf-AuNP) against pepsin, which is a protease.
Figure 7B:
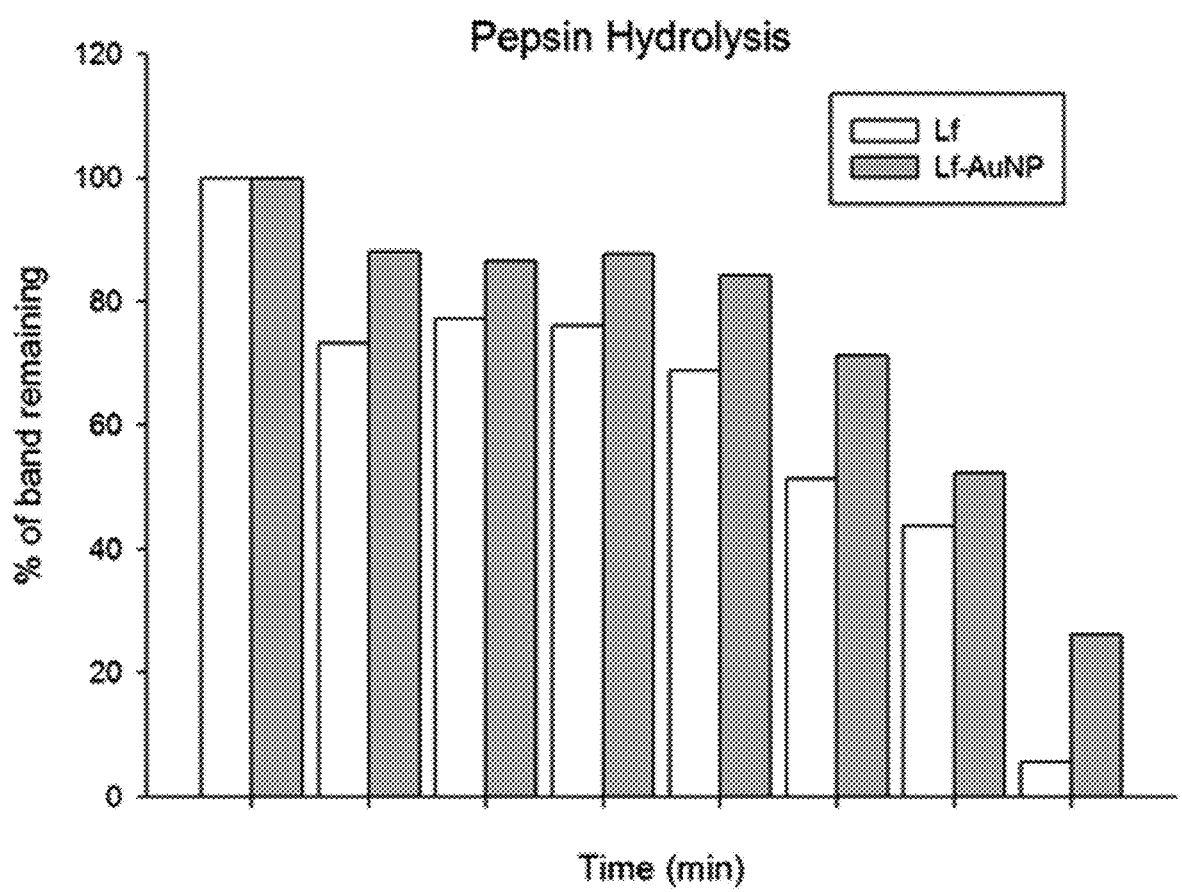
FIG. 7b is the result quantitatively showing Pepsin Hydrolysis assay results of lactoferrin (Lf) and gold nanoparticle complexes (Lf-AuNP).

As a result, as shown in FIGS. 7a and 7b, it could be confirmed that the lactoferrin bound to the gold nanoparticle complex has superior stability against pepsin as compared to the unbound lactoferrin (Lf).

Example 4: Assessment of Cytotoxicity

The gold nanoparticle complex becomes a target of the lactoferrin receptor present in the small intestine, enters into the blood through the endothelial cells of the small intestine, and then the gold nanoparticle complex present in the blood is targeted to brain tumor tissues to be accumulated in brain tissues or blood vessels. Thus, in this example, cytotoxicity tests were performed on small intestinal endothelial cells and vascular endothelial cells.

4-1. Evaluation of Toxicity to Small Intestinal Endothelial Cells

To confirm cytotoxicity of the gold nanoparticle complex in small intestinal endothelial cells, cellular changes were observed by an electron microscope and the number of viable cells was quantitatively analyzed through cell cytotoxicity assay. Specifically, Caco-2 cells in a 96-well plate were cultured in an incubator at a concentration of $5 \times 10^3$/well for 24 hours, and the cultured cells were treated with the gold nanoparticle complex at a concentration of 800 μg/100 μl, and then reacted in the incubator for 24 hours. Then, the gold nanoparticle complex was washed, treated with media (100 μl) and EZ-Cytox (10 μl) as a cell cytotoxicity assay kit and reacted in the incubator for about 4 hours. To evaluate cytotoxicity, the absorbance at 450 nm was measured by using a plate reader, and as the control group, the untreated group (Con) was used and as the comparative group, the general gold nanoparticle treated group (AuNP) was used.

Figure 8A:
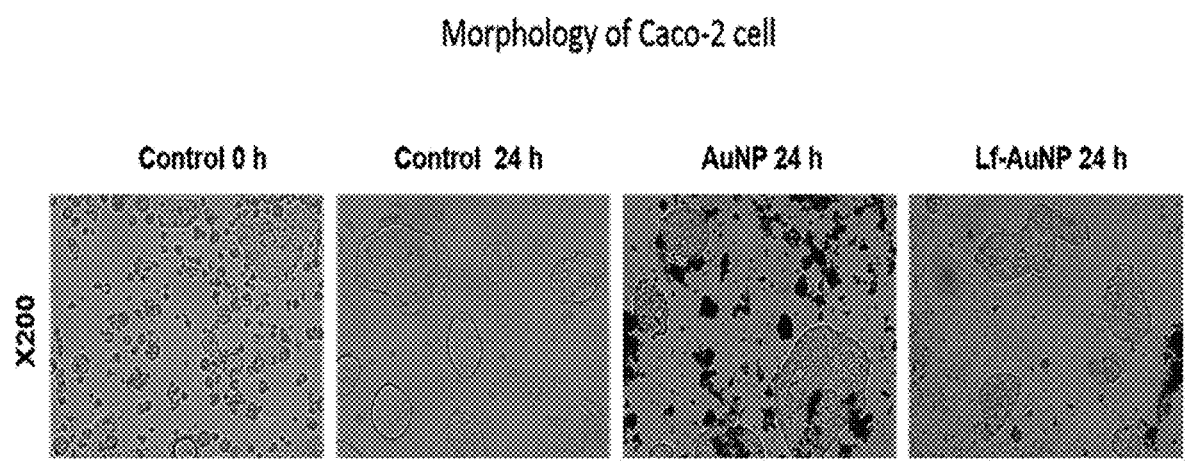
FIG. 8a is the result of observing changes in cells by an electron microscope after treatment of small intestinal endothelial cells with gold nanoparticle complexes (Lf-AuNP).
Figure 8B:
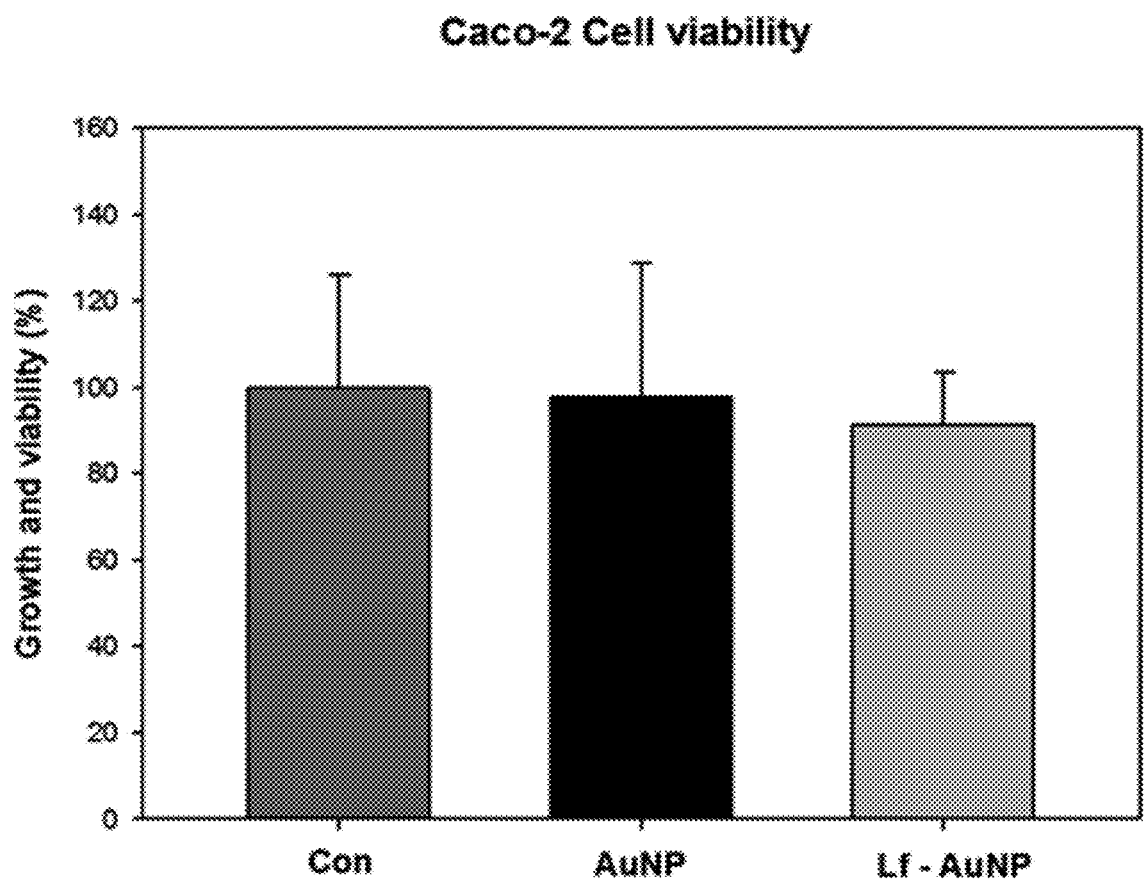
FIG. 8b is the result of quantitatively analyzing cell survival rate through cell cytotoxicity assay after treatment of small intestinal endothelial cells with gold nanoparticle complexes (Lf-AuNP).

As a result, as shown in FIG. 8, when the state of the cells treated with the gold nanoparticle complex of the present invention was compared with the control group and the comparative group, there was no difference at all (see FIG. 8a), and as a result of quantitatively analyzing the number of viable cells, it was confirmed that as in the above result, the viability of small intestinal endothelial cells was not reduced at all (see FIG. 8b), so that it could be confirmed that the gold nanoparticle complex of the present invention did not show cytotoxicity to small intestinal endothelial cells.

4-2. Evaluation of Toxicity to Vascular Endothelial Cells

To confirm cytotoxicity of the gold nanoparticle complex in vascular endothelial cells, cellular changes were observed by an electron microscope and the number of viable cells was quantitatively analyzed through cell cytotoxicity assay. Specifically, human umbilical vein endothelial cells (HUVEC) in a 96-well plate were cultured in an incubator at a concentration of $5 \times 10^3$/well for 24 hours, and the cultured cells were treated with the gold nanoparticle complex at a concentration of 800 μg/100 μl, and then reacted in the incubator for 24 hours. Then, the gold nanoparticle complex was washed, treated with media (100 μl) and EZ-Cytox (10 μl) as a cell cytotoxicity assay kit and reacted in the incubator for about 4 hours. To evaluate cytotoxicity, the absorbance at 450 nm was measured by using a plate reader, and as the control group, the untreated group (Con) was used and as the comparative group, the general gold nanoparticle treated group (AuNP) was used.

Figure 9A:
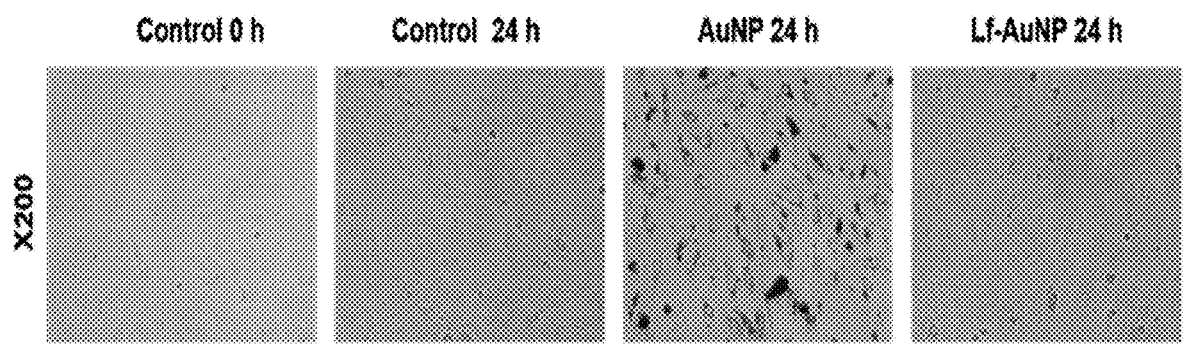
FIG. 9a is the result of observing changes in cells by an electron microscope after treating vascular endothelial cells with gold nanoparticle complexes (Lf-AuNP).
Figure 9B:
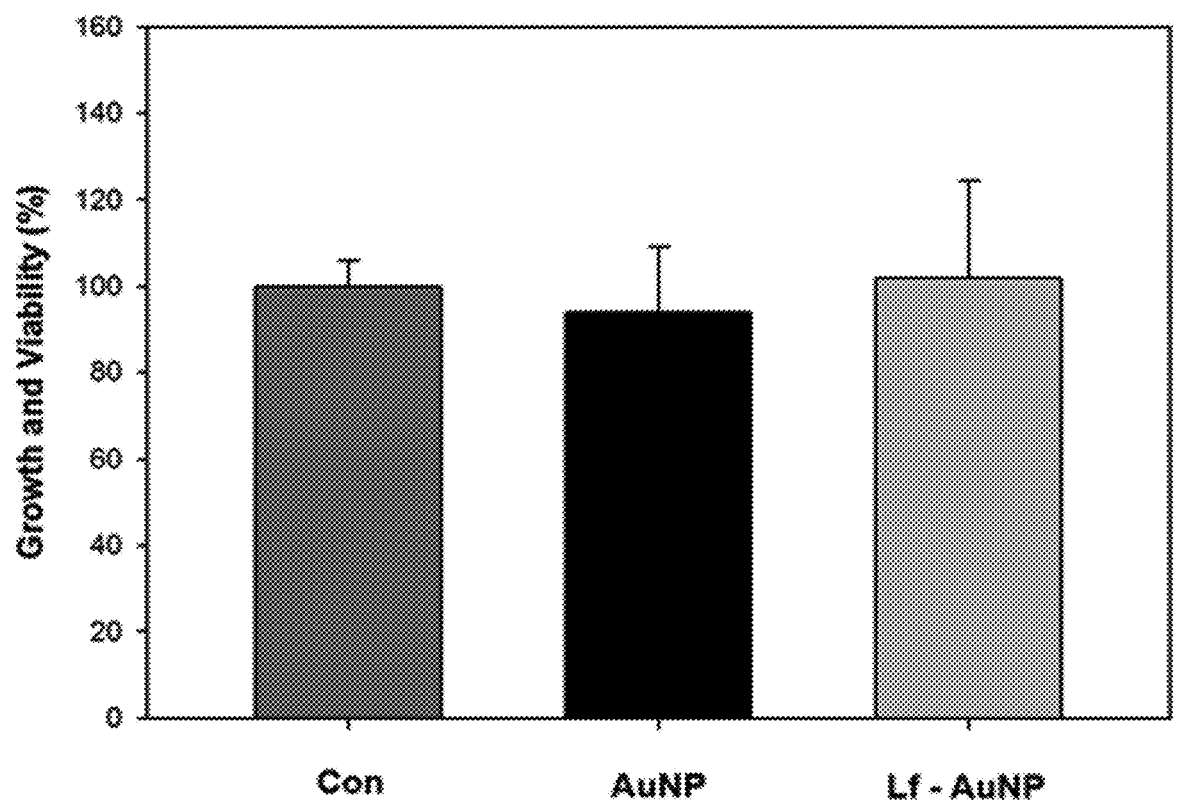
FIG. 9b is the result of quantitatively analyzing cell survival rate through cell cytotoxicity assay after treating vascular endothelial cells with gold nanoparticle complexes (Lf-AuNP).
Figure 10:
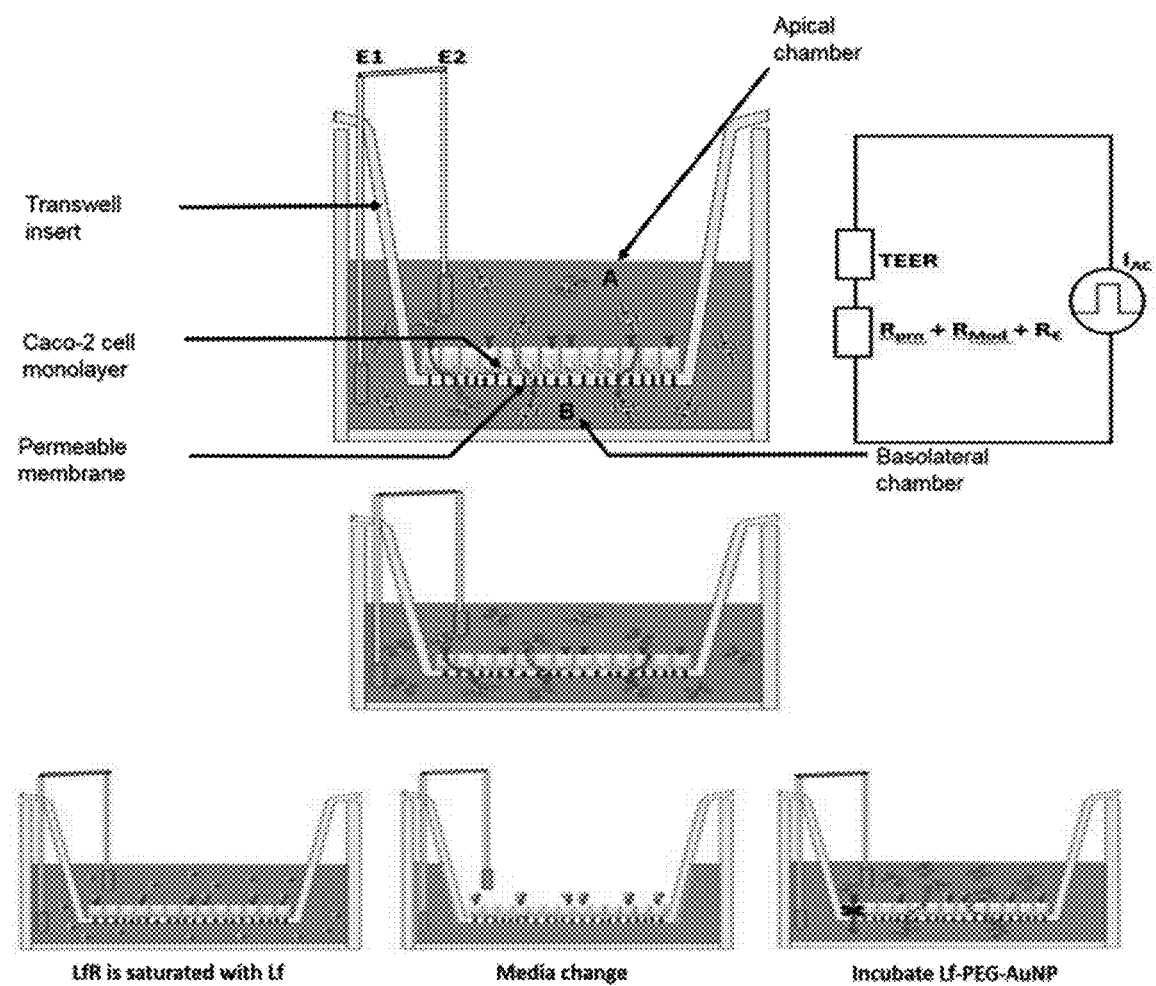
FIG. 10 is a view schematically showing the construction and procedure of the Caco-2 cell permeability assay for evaluating the oral absorption rate of gold nanoparticle complexes.

As a result, as shown in FIG. 9, when the state of the cells treated with the gold nanoparticle complex of the present invention was compared with the control group and the comparative group, there was no difference at all (see FIG. 9a), and as a result of quantitatively analyzing the number of viable cells, it was confirmed that as in the above result, the viability of vascular endothelial cells was not reduced at all (see FIG. 9b), so that it could be confirmed that the gold nanoparticle complex of the present invention did not show cytotoxicity to vascular endothelial cells.

Example 5: Identification of Oral Absorption Rate Enhancement Effect of Gold Nanoparticle Complex 5-1. Measurement of Transmittance of Gold Nanoparticle Complex to Small Intestinal Endothelial Cells Via Trans-Epithelial Electrical Resistance (TEER)

In this example, Caco-2 cell permeability assay was performed to confirm the oral absorption rate of gold nanoparticle complex in vitro in small intestinal endothelial cells. Caco-2 cells were cultured at a concentration of $2 \times 10^3$ in a 0.4 μm pore size insert, and the trans-epithelial electrical resistance (TEER) values were measured using EVOM$^2$ (epithelial volt ohm meter) until tight junctions were formed. Then, the insert was treated with the gold nanoparticle complex at a concentration of 800 μg/100 μl, and then the TEER values were measured every 20 minutes using EVOM$^2$. Specifically, as shown in FIG. 9, when the gold nanoparticle complex moves from the apical side (A) to the basolateral side (B), the tight junction between Caco-2 cells spreads and simultaneously the TEER value decreases. Therefore, the oral absorption rate was evaluated in vitro through change of the TEER values.

Figure 11:
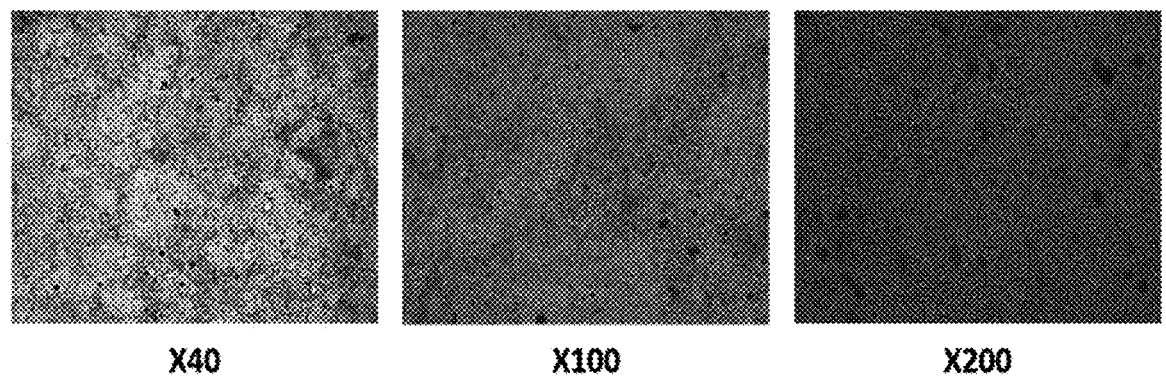
FIG. 11 is the result of observing the presence or absence of formation of bonds between small intestine endothelial cells by an electron microscope, when formation of a tight junction is expected through the TEER value.

First, as a result of observing Caco-2 cells on exhibiting the TEER value, in which the tight junction is formed, by an electron microscope, as shown in FIG. 11, complicated networks were formed through intercellular band-like structures, which means that Caco-2 cells are bound to tight junctions.

Figure 12:
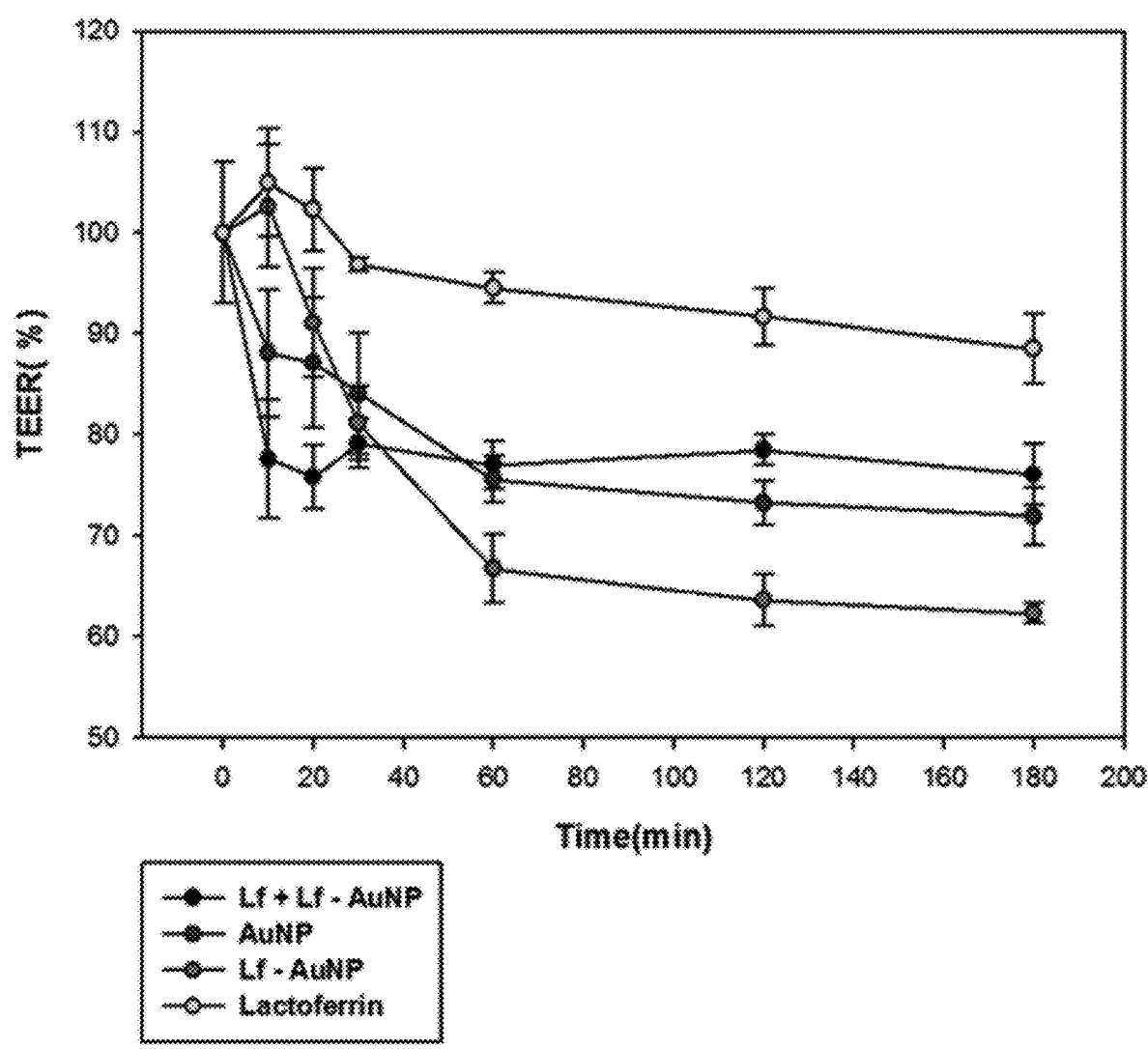
FIG. 12 is the result of comparing the TEER values of gold nanoparticle complexes (Lf-AuNP) through Caco-2 cell permeability assay with those of the group (AuNP) treated with general gold nanoparticles, the group (Lactoferrin) treated with only lactoferrin, and the group (Lf+Lf-AuNP) treated with gold nanoparticle complexes after binding lactoferrin and lactoferrin receptor.

In addition, as shown in FIG. 12, when Caco-2 cells formed by tight junctions as above were treated with general gold nanoparticles (AuNP), the TEER value was about 73%, and in the case of the gold nanoparticle complex (Lf-AuNP), the TEER value decreased to about 62%. Particularly, in the case of treating them with only lactoferrin, the TEER value was reduced by about 10%, which is similar to the difference in TEER values of general gold nanoparticles and the gold nanoparticle complex, and thus it could be seen that the oral absorption rate was increased by the effect of lactoferrin. Besides, in order to confirm again that the oral absorption rate enhancement effect is due to lactoferrin, Caco-2 cells were treated with only lactoferrin for 3 hours to be sufficiently bound to the lactoferrin receptor, and then treated with the gold nanoparticle complex (Lf+Lf-AuNP) in the same condition as above, so that it could be confirmed that the oral absorption enhancement effect is due to the lactoferrin receptor and lactoferrin by confirming no difference in the TEER value with the general gold nanoparticle treated group.

5-2. Identification of Absorption of Gold Nanoparticle Complexes on Small Intestinal Endothelial Cells In this example, absorption of gold nanoparticle complexes on small intestinal endothelial cells was confirmed in vitro. Tight junctions were formed by culturing Caco-2 cells in 100π culture dish to reach $8.8 \times 10^6$ cells. Thereafter, the cells were treated with the gold nanoparticle complex at a concentration of 800 μg/100 μl, and then cultured for 18 hours, washed three times, and separated through trypsin/EDTA. Then, after 4% formaldehyde fixation and also resin fixation of the cells, tissue slices prepared by ultramicrotome (EM UC7, Germany) were observed with an 80 kV Transmission Electron Microscope (JEM1010, Japan).

Figure 13:
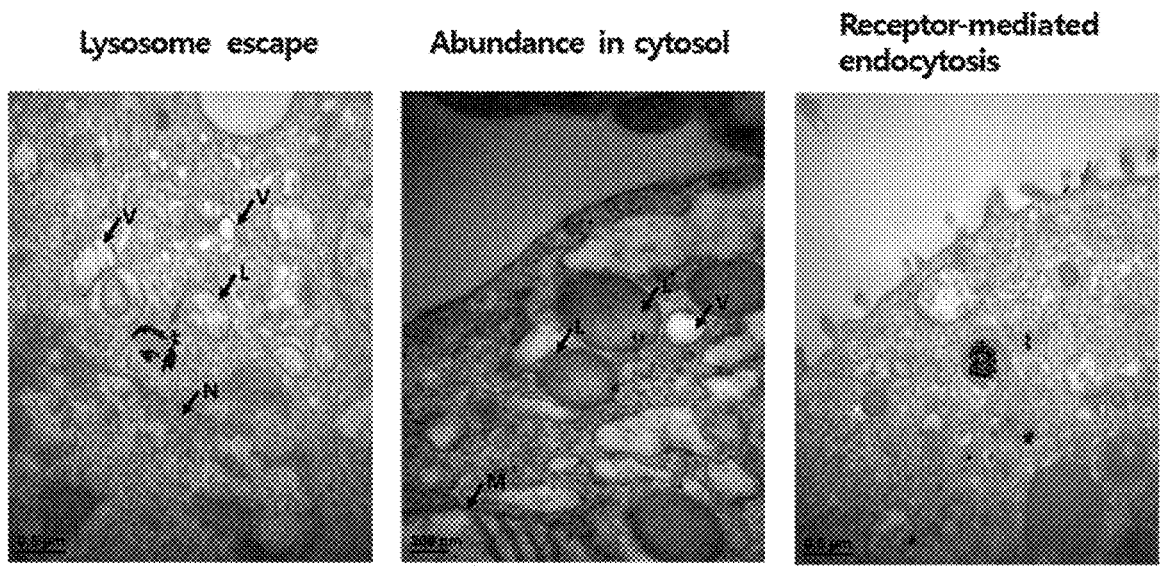
FIG. 13 is the result of confirming gold nanoparticle complex (Lf-AuNP) intake of small intestinal endothelial cells (Caco-2 cells) through lactoferrin receptor mediated transfer and passive transport permeating intracellular tight junction by a Bio-TEM Electron microscope).

As shown in FIG. 13, the uptake of the gold nanoparticle complex of the endothelial cells mediated by lactoferrin receptors could be observed through the lysosome escape phenomenon and the vesicle invagination of the gold nanoparticle complex around the cell membrane. In addition, the intracellular uptake through the passive transport penetrating intracellular tight junctions could be confirmed by confirming a large amount of gold nanoparticles in cytoplasm other than organelles.

Figure 14:
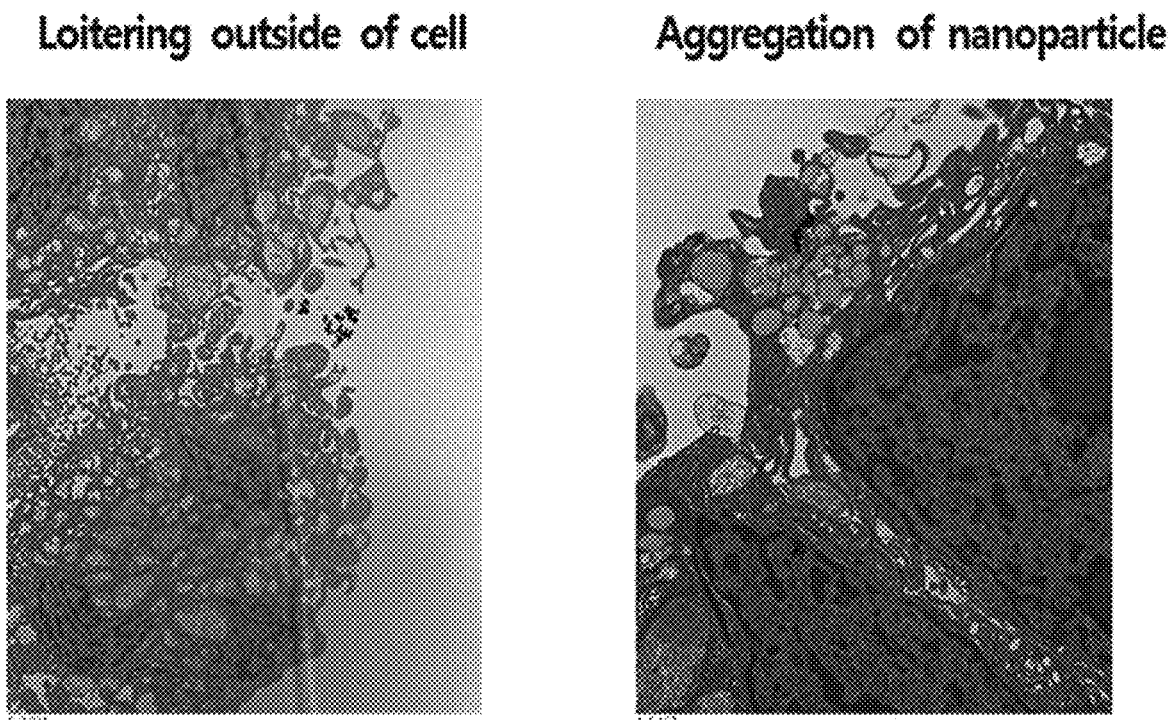
FIG. 14 is the result of confirming gold nanoparticle (AuNP) intake of small intestinal endothelial cells (Caco-2 cells) by a Bio-TEM (transmission electron microscope).

On the other hand, in the case of gold nanoparticles, intracellular uptake of gold nanoparticles (AuNP) mediated by lactoferrin receptors of small intestinal endothelial cells could not be confirmed, as shown in FIG. 14.

Example 6: Identification of Brain Tumor Targeting Enhancement Effect Through Oral Administration of Gold Nanoparticle Complex In this example, absorption of the gold nanoparticle complex on brain tumor cells (U87MG) was confirmed in vitro. Tight junctions were formed by culturing U87MG cells in 100 π culture dish to reach $8.8 \times 10^6$ cells. Thereafter, the cells were treated with the gold nanoparticle complex at a concentration of 800 μg/100 μl, and then cultured for 18 hours, washed three times, and separated through trypsin/EDTA. Then, after 4% formaldehyde fixation and also resin fixation of the cells, tissue slices prepared by ultramicrotome (EM UC7, Germany) were observed with an 80 kV Transmission Electron Microscope (JEM1010, Japan).

Figure 15:
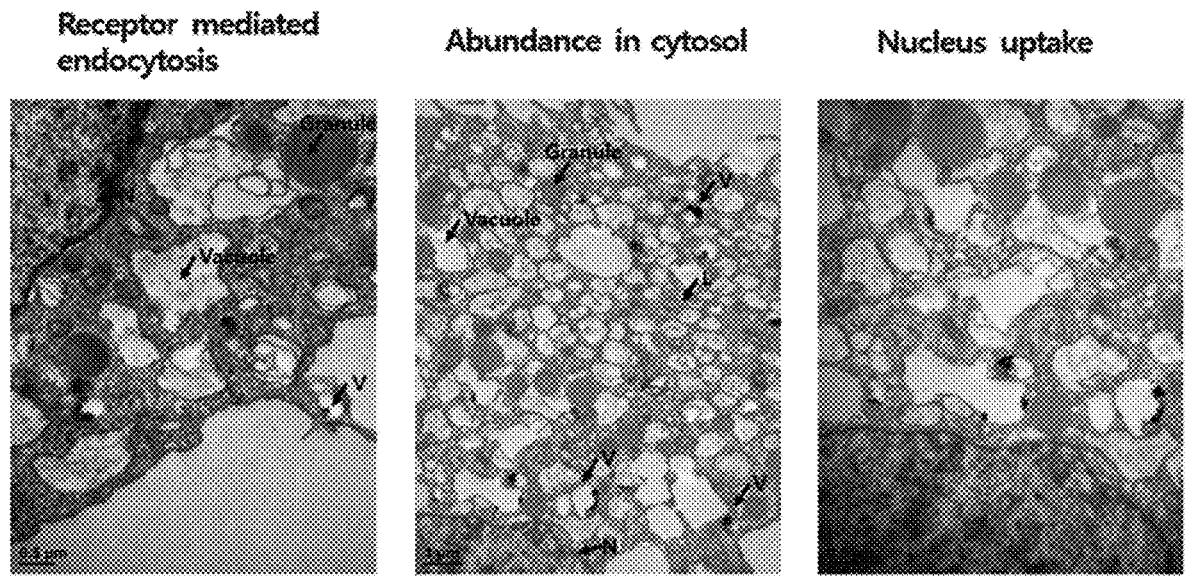
FIG. 15 is the result of confirming gold nanoparticle complex (Lf-AuNP) intake of brain tumor cells (U87MG) through lactoferrin receptor mediated transfer and passive transport permeating intracellular tight junction by a Bio-TEM Electron microscope).
Figure 16:
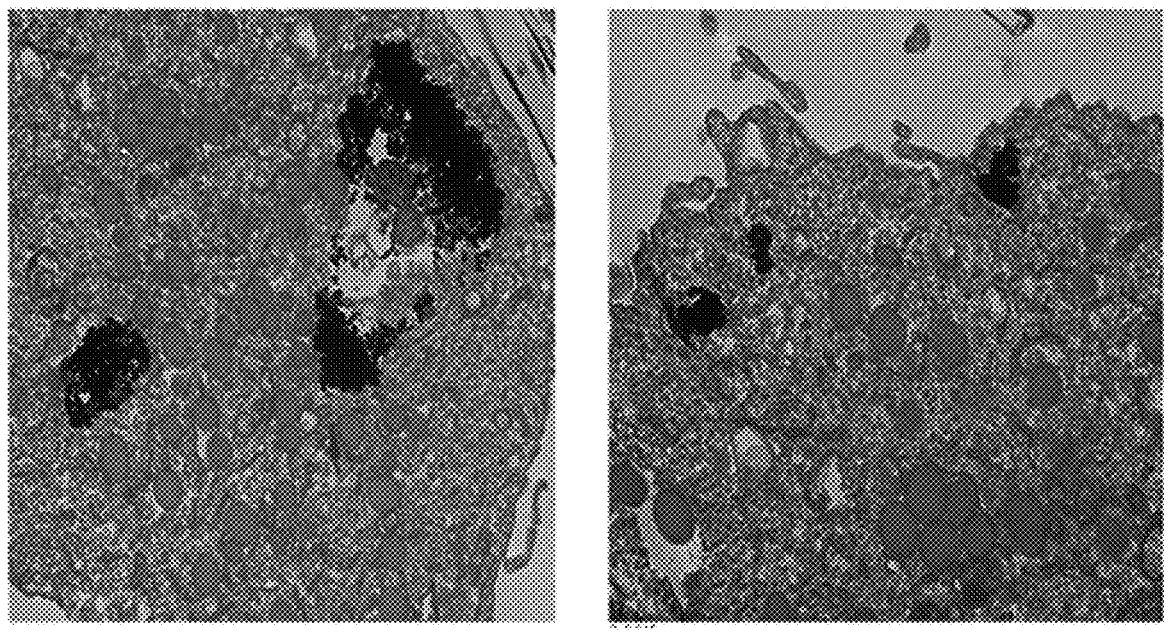
FIG. 16 is the result of confirming gold nanoparticle (AuNP) intake of brain tumor cells (U87MG) by a Bio-TEM (transmission electron microscope).

As a result, as shown in FIG. 15, the uptake of the gold nanoparticle complex of the endothelial cells mediated by lactoferrin receptors could be observed through the lysosome escape phenomenon and the vesicle invagination of the gold nanoparticle complex around the cell membrane. In addition, the intracellular uptake through the passive transport penetrating intracellular tight junctions could be confirmed by confirming a large amount of gold nanoparticles in cytoplasm other than organelles. From the results, it could be seen that the gold nanoparticle complex ingested to the small intestinal endothelial cells through oral administration could be delivered to the brain tumor tissues via the lactoferrin receptor and it is determined that since the gold nanoparticle complex has a size of about 5 nm, it can be transferred to the cellular nuclei as well as the cytoplasm.

Figure 18:
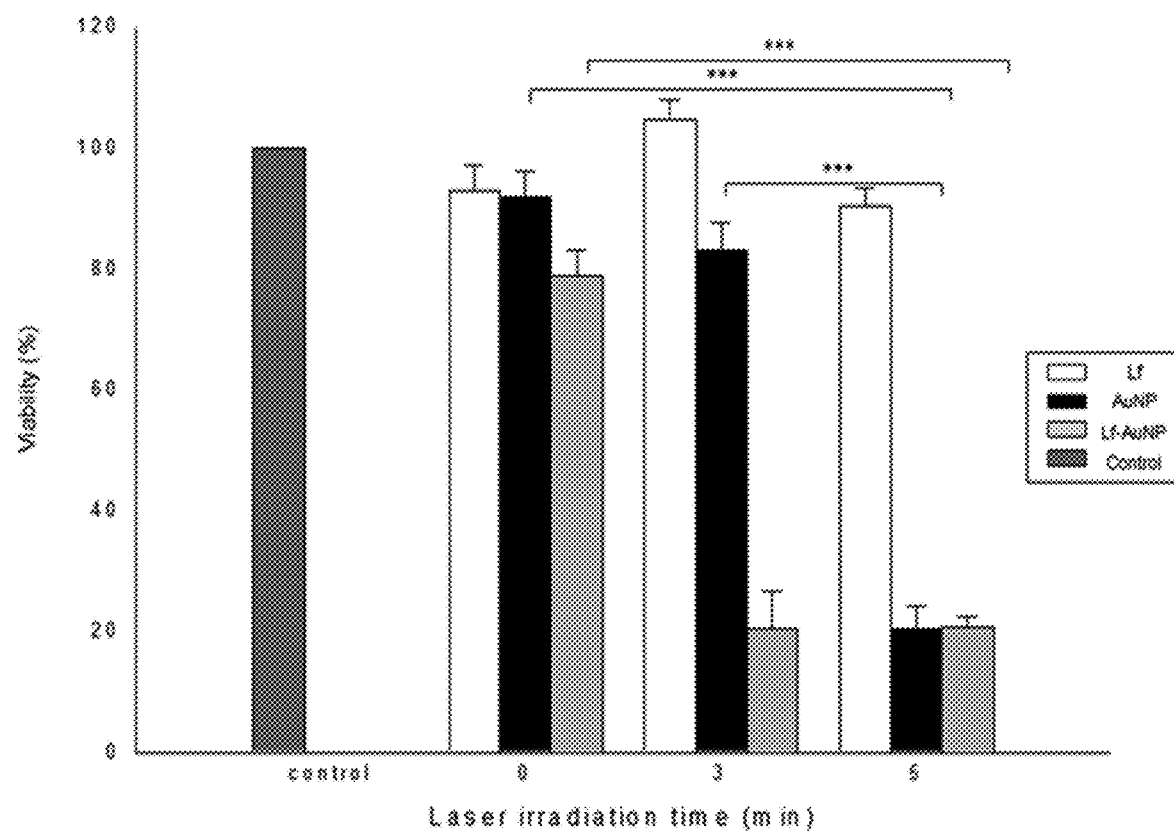
FIG. 18 is the result of quantitatively analyzing cell survival rate through cell cytotoxicity assay after irradiating brain tumor cells (U87MG) of the group (Lactoferrin) treated with only lactoferrin, the group (AuNP) treated with only gold nanoparticles, and the group (Lf-AuNP) treated with gold nanoparticle complexes, with light having a wavelength of 532 nm for 0, 3 and 5 minutes.

Example 7: Identification of Photothermal Therapeutic Effect of Gold Nanoparticle Complex on Brain Tumor Cells In Vitro As the photothermal therapeutic effect using gold nanoparticle complex and near infrared wavelength band (532 nm) laser, cell death of brain tumor cells was confirmed through cell cytotoxicity assay. Specifically, brain tumor cells (U87MG) in a 96-well plate were cultured in an incubator at a concentration of $5\times10^3$/well for 24 hours, and the cultured cells were treated with the gold nanoparticle complex at a concentration of 500 µg/ml, and then reacted in the incubator for 18 hours. Then, the gold nanoparticle complex was washed twice, irradiated with the laser for 0.3 and 5 minutes, and then washed once again. Thereafter, the cells were treated with media (100 µl) and EZ-Cytox (10 µl) as a cell cytotoxicity assay kit and reacted in the incubator for about 1 hour. To quantitatively analyze the number of viable cells, the absorbance at 450 nm was measured using a plate reader, and as the control group, the untreated group (Con) was used and as the comparative group, the group treated with 8.1 µg/ml of lactoferrin and the group treated with 90 µg/ml of gold nanoparticles, in consideration of the binding ratio of gold nanoparticle complex, were used (see FIG. 18).

Figure 17:
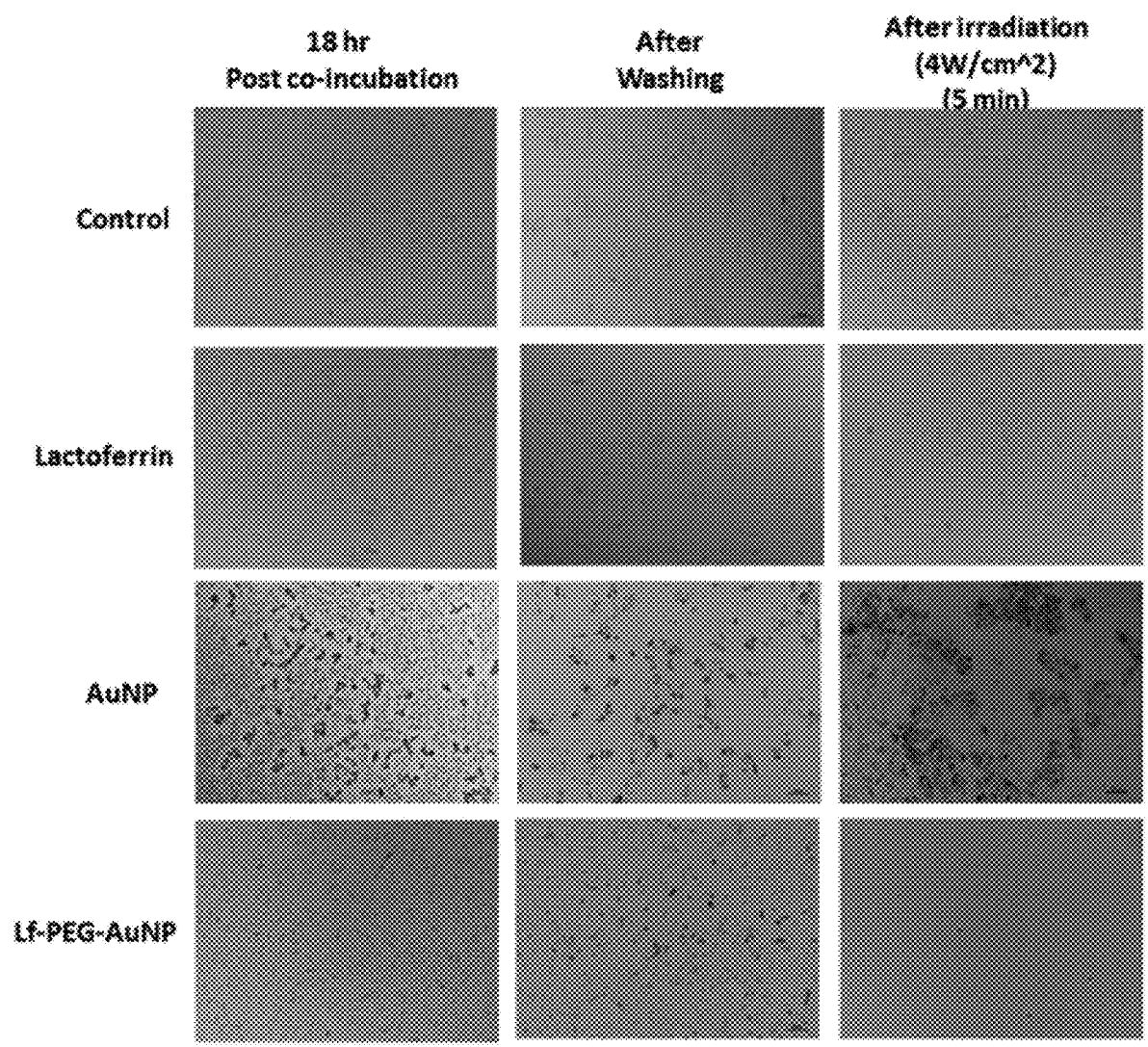
FIG. 17 is the result of confirming each cell type by an optical microscope after irradiating brain tumor cells (U87MG) of the group (Lactoferrin) treated with only lactoferrin, the group (AuNP) treated with only gold nanoparticles, and the group (Lf-AuNP) treated with gold nanoparticle complexes, with light having a wavelength of 532 nm for 0, 3 and 5 minutes.

As a result, as shown in FIG. 17, in the group treated with the gold nanocomplex, the survival rate of the brain tumor cells was also reduced by 20% in a short irradiation time of 3 minutes, as compared with the other comparative groups, whereas in the group treated with general gold nanoparticles, cell death was observed to the same extent as above through laser irradiation of 5 minutes.

Taken together with the above experimental results, it can be seen that the intake increase of the lactoferrin receptor-mediated gold nanoparticle complex to the brain tumor cells leads to the improvement of the photothermal therapeutic effect on brain tumor cells, that is, the cell killing effect.

Example 8: Identification of Oral Absorption of Gold Nanocomplex Using Animal Model This example was intended to confirm absorption in the small intestine after oral administration of the gold nanoparticle complex using an animal model. Specifically, a Balb/c rat was allowed to remain in its fasted state for 6 hours, and then the gold nanoparticle complex was orally administered thereto at a concentration of 60 mg/kg. After 2.5 hours, the rat was sacrificed and exsanguinated, and after extracting the small intestine and then fixing its duodenum, jejunum and ileum separately with 4% formaldehyde and again resin-fixing them, tissue slices prepared by ultramicrotome (EM UC7, Germany) were observed with an 80 kV Transmission Electron Microscope (JEM1010, Japan).

Figure 19:
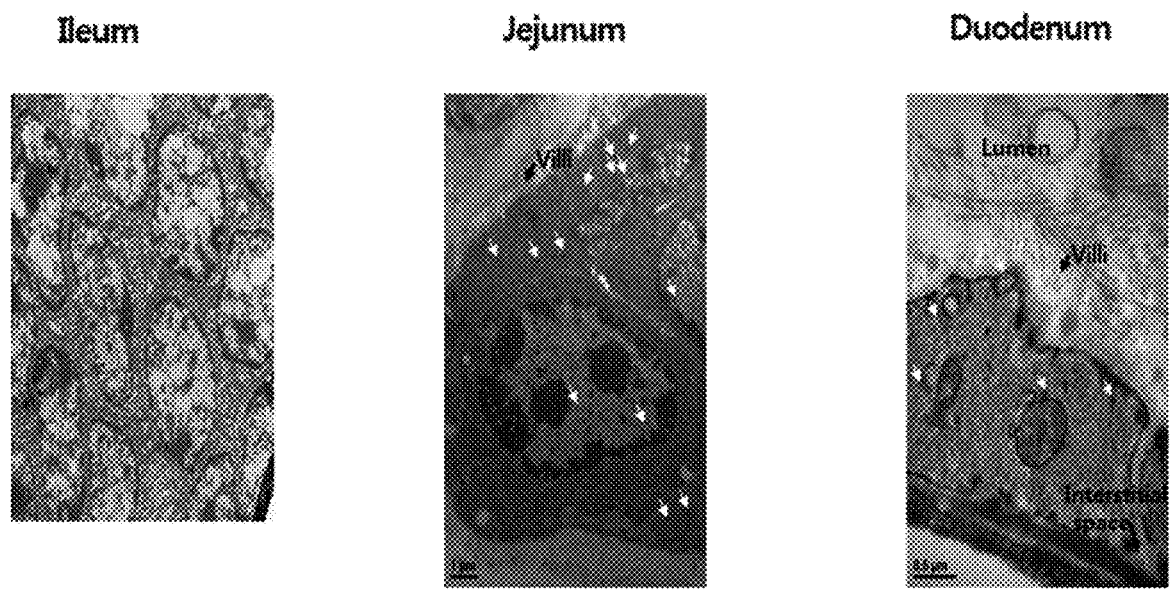
FIG. 19 is the result of confirming absorption in ileum, jejunum and duodenum by a Bio-TEM (transmission electron microscope) after oral administrating gold nanoparticle complexes (Lf-AuNP) to an animal model.

As a result, as shown in FIG. 19, a large amount of gold nanocomplex was detected in the duodenum, ileum and jejunum of the small intestine, and thus the selective absorption of the gold nanocomplex could be confirmed. These results suggest that the orally administered gold nanoparticle complex can enter into the blood through the capillaries of the small intestine and be transferred to the brain tumor tissues through the systemic circulation.

Example 9: Identification of Targeting Effect of Brain Tumor Tissues Using Animal Model This example was intended to confirm the brain tumor targeting effect of the gold nanoparticle complex using a brain tumor animal model. Specifically, U87MG cells cultured in DMEM medium adding 10% FBS and 1% antibiotics were collected in PBS without antibiotics. Thereafter, a 5 to 7 week old nude mouse was anesthetized with isoflurane and fixed with an ear bar in a stereotaxic instrument. After the scalp of the surgical site was incised, a hole was made using a sterile drill at 2 mm to the right and 2 mm to the downward direction of the bregma. Then, $1\times10^6$ U87MG cells were injected into a 26 G Hamilton syringe through the hole (1 µl/min), and after injection, the brain tumor animal model was established by sealing the hole with bone wax, suturing it and closing the scalp.

9-1. Identification of Brain Tumor Targeting Effect Through ICP-MS

The gold nanoparticle complex (200 µl) at a concentration of 60 mg/kg was orally absorbed via oral gavage to the brain tumor animal model. After 24 hours, the brain tumor animal model was exsanguinated, the brain was extracted, and the amount of gold nanoparticles present in the obtained blood and brain was measured through ICP-MS. As the comparative group, a group (AuNP) orally administered with general gold nanoparticles at a concentration of 11 mg/kg in consideration of the binding ratio of gold nanoparticles in the gold nanoparticle complex was used. On the other hand, in order to confirm the brain tumor targeting effect of the gold nanoparticles due to the difference in drug administration modes, the gold nanoparticle complex was administered intravenously 10 times at a concentration of 1 mg/kg. As the comparative group, a group (AuNP) intravenously administered with general gold nanoparticles at a concentration of 0.18 mg/kg was used.

Figure 20:
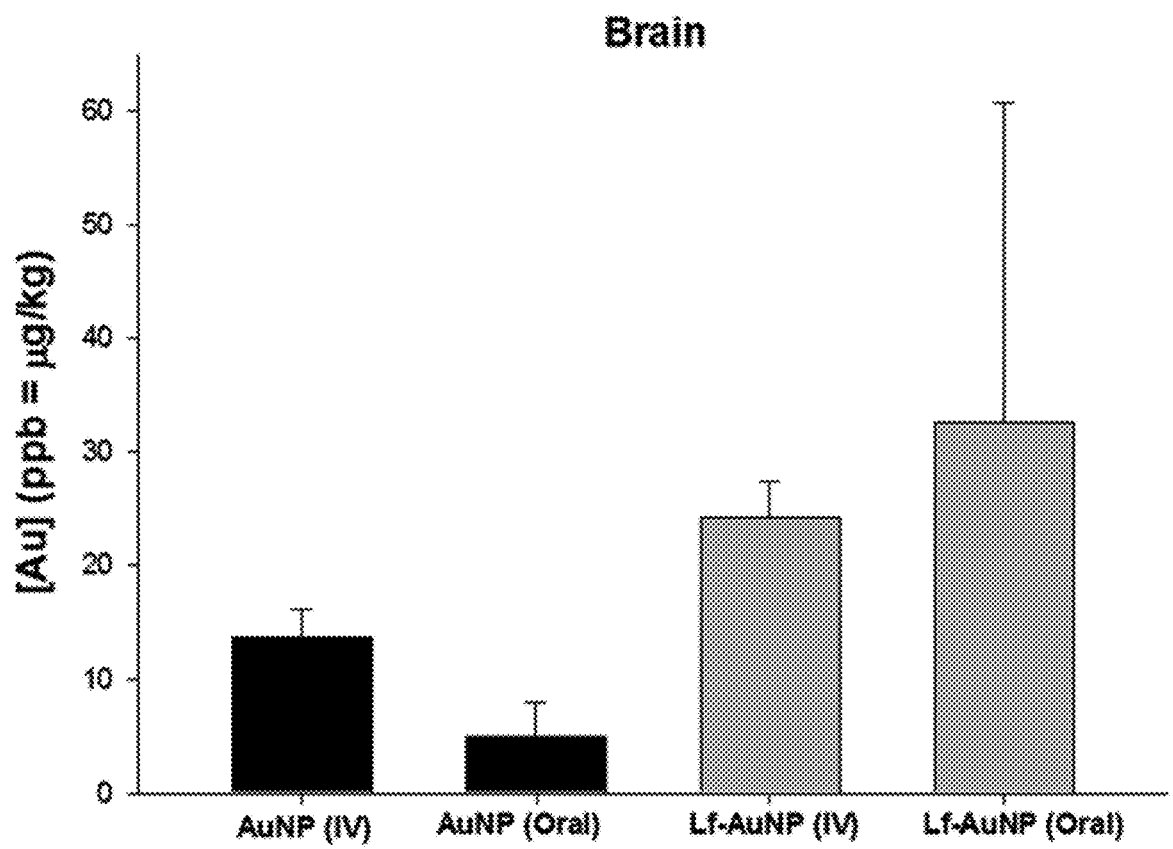
FIG. 20 is the result of comparing the amounts of gold nanoparticles present in brain tissues after oral administration and intravenous administration of gold nanoparticles (AuNP) and gold nanoparticle complexes (Lf-AuNP) to a brain tumor animal model.

As a result, as shown in FIG. 20, it could be seen that in the control group treated with general gold nanoparticles through intravenous or oral administration, a small amount of gold nanoparticles was present in the brain due to the blood brain barrier (BBB) destruction according to formation of brain tumors and the enhanced permeability and retention effect (EPR), but it could be seen that in the case of treating with the gold nanoparticle complex through intravenous or oral administration, gold nanoparticles were accumulated at least 5-6 times more than such a control group. This indicates that a large amount of gold nanoparticles was delivered to the brain tissues via lactoferrin receptor mediated transcytosis and an increased half-life effect by PEG. In addition, the differences in brain tumor targeting according to the drug administration methods can be confirmed. Specifically, in the group treated with general gold nanoparticles, intravenous administration showed a higher accumulation amount than that of the case by oral administration. On the other hand, in the case of the gold nanoparticle complex of the present invention, oral administration showed higher efficiency. Such a result is a result attributable to enhancing the half-life of the whole complex comprising the gold nanoparticles and improving the bioavailability through all of the aforementioned constructions. That is, it is expected that the targeting enhancement effect of the orally administered gold nanoparticle complex on brain tumor tissues can improve the photothermal or photodynamic therapeutic effect on brain tumors.

9-2. Identification of Brain Tumor Targeting Effect Through Immunohistochemical Staining (IHC Staining)

To the brain tumor animal model, the gold nanoparticle complex (200 µl) at a concentration of 60 mg/kg was orally administered via oral gavage. After 24 hours, the brain tumor animal model was exsanguinated, the brain was extracted, and the obtained brain tissues were fixed with 4% paraformaldehyde for 2 days. Then, the tissues were placed in a Leica TP1020 Semi-enclosed Benchtop Tissue Processor to complete processes of interstitial washing, dewatering, transparentizing and paraffin-penetrating, and then the tissues completing paraffin penetration were placed in a base mold to facilitate the production of flakes, and hardened by dispensing paraffin. Then, the slices containing tissues were prepared to a thickness of 4 μm via the slicing process using a paraffin rotation type slicer, Leica RM2145 Microtome. For the slices, deparaffinizing, wetting and washing processes were carried out. For blocking sera, the slice was treated with a mixture, in which 80% Phosphate Buffered Saline Tween-20 (PBST) and 20% Goat Serum were mixed, by 50 μl per slide and adhered with a paraffin film. After 30 minutes, the slice was treated with a dilution, in which a primary antibody and lactoferrin were diluted in the mixture of PBST and goat serum at a ratio of 1:100, by 50 μl per slide, and reacted in a state where the paraffin film was closely adhered at 4° C. for 12 hours. The next day, the slice was treated with a dilution, in which a secondary antibody, goat anti-rabbit, containing a fluorescent substance, was diluted in PBS at a ratio of 1:100, by 50 μl per slide, and reacted for 1 hour. Then, after a mounting process, the slice was observed via a fluorescence microscope.

As the comparative group, a group (AuNP) orally administered with general gold nanoparticles at a concentration of 11 mg/kg and a group (Lf) orally administered with lactoferrin at a concentration of 1.7 mg/kg, in consideration of the binding ratio of gold nanoparticles in the gold nanoparticle complex, were used. On the other hand, in order to confirm the brain tumor targeting effect of the gold nanoparticles due to the difference in drug administration modes, the gold nanoparticle complex was administered intravenously 10 times at a concentration of 1 mg/kg. As the comparative group, a group (AuNP) intravenously administered with general gold nanoparticles at a concentration of 0.18 mg/kg and a group (Lf) intravenously administered with lactoferrin at a concentration of 0.017 mg/kg, in consideration of the binding ratio of gold nanoparticles in the gold nanoparticle complex, were used.

Figure 21A:
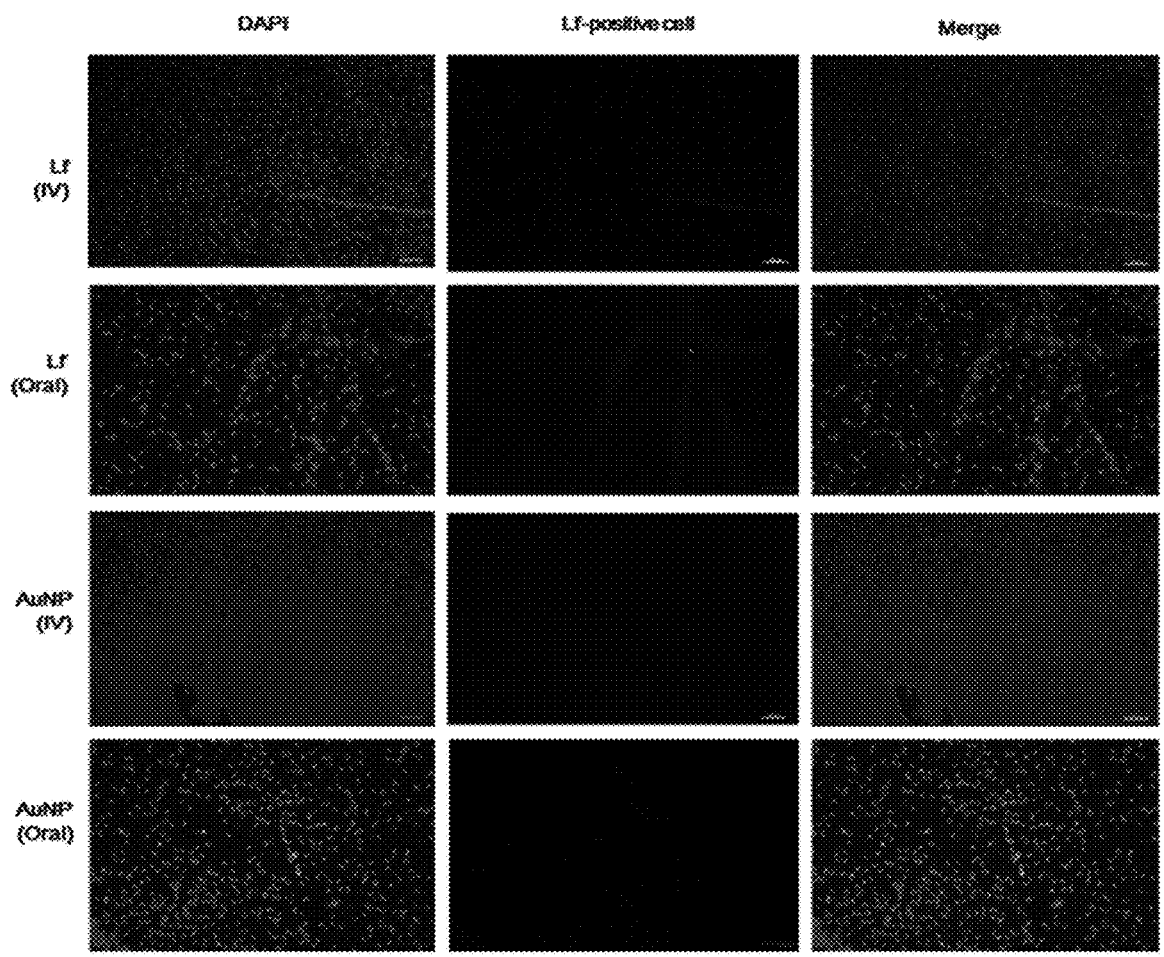
FIG. 21a is the result of confirming distribution in brain tumor tissues by immunohistochemical stain and a fluorescence microscopy after oral administration and intravenous administration of lactoferrin or gold nanoparticles (AuNP).
Figure 21B:
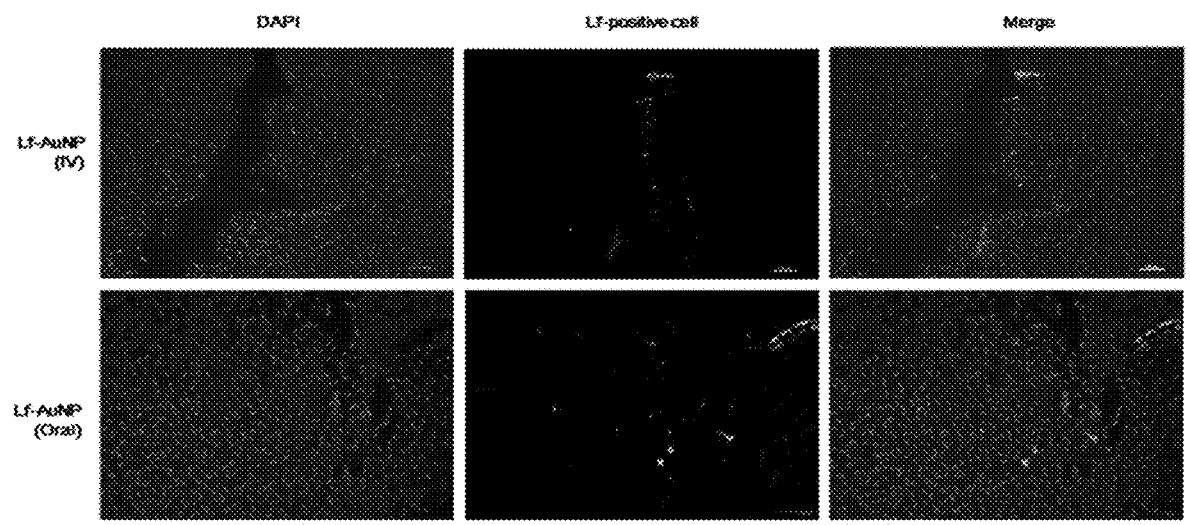
FIG. 21b is the result of confirming distribution in brain tumor tissues by immunohistochemical stain and a fluorescence microscopy after oral administration and intravenous administration of gold nanoparticle complexes (Lf-AuNP).
Figure 21C:
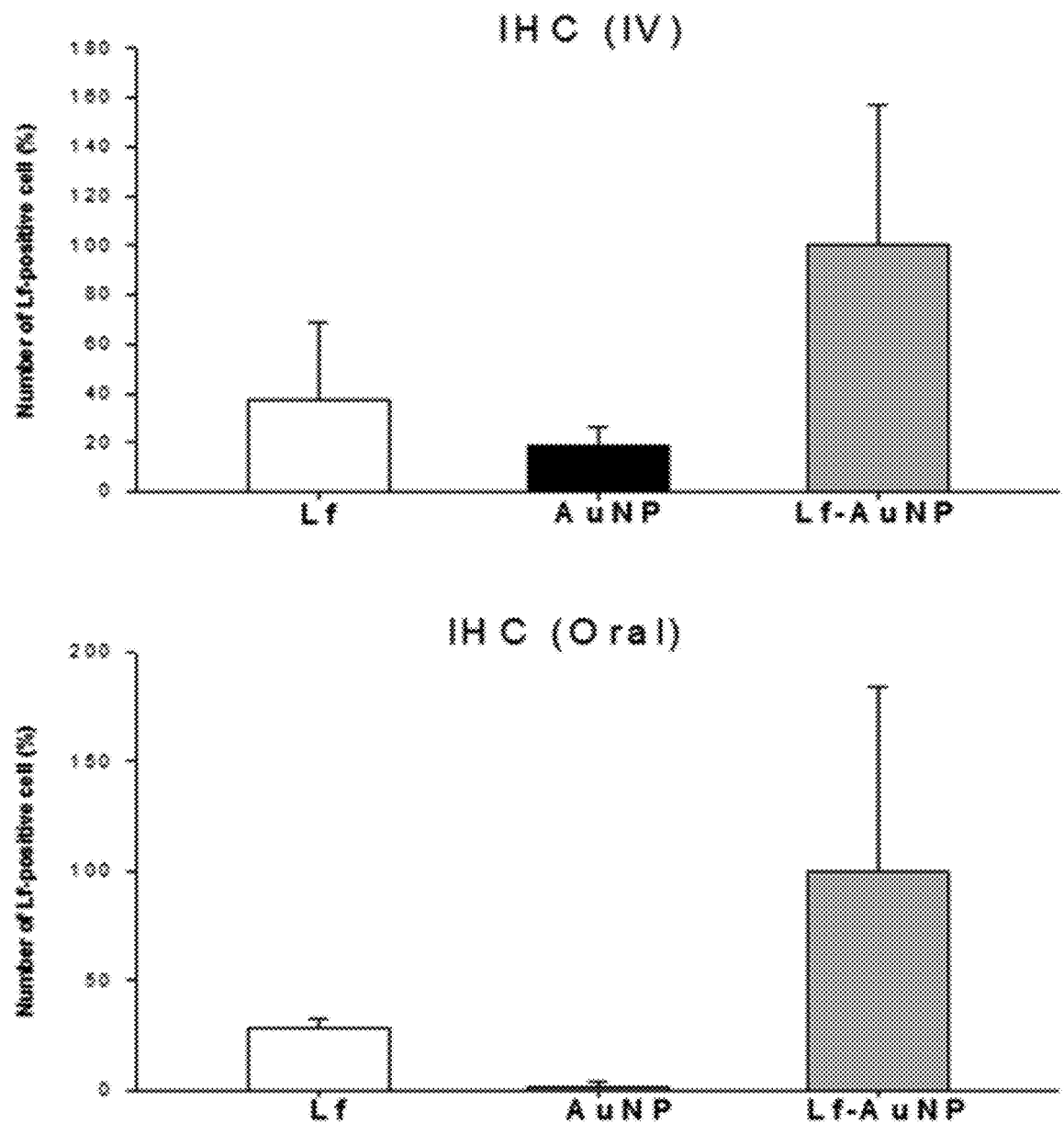
FIG. 21c is the result of quantitatively confirming distribution in brain tumor tissues after oral administration and intravenous administration of lactoferrin, gold nanoparticles (AuNP), or gold nanoparticle complexes (Lf-AuNP).

As a result, as shown in FIG. 21, the most fluorescence was observed in the group treated with the gold nanoparticle complex. This is a result attributable to the fact that the reaction between the lactoferrin, which is a target antigen contained in the gold nanoparticle complex, and the lactoferrin receptor, which is abundantly expressed in the brain tumor tissues, is superior to the comparative group. From this, the targeting effect of the brain tumor tissues according to the present invention could be confirmed.

9-3. Identification of Brain Tumor Targeting Effect Through Bio-TEM

To the brain tumor animal model, the gold nanoparticle complex (200 μl) at a concentration of 60 mg/kg was orally administered via oral gavage. After 24 hours, the brain tumor animal model was exsanguinated, and the brain was extracted, fixed with 4% formaldehyde, and again resin-fixed, and then tissue slices prepared by ultramicrotome (EM UC7, Germany) were observed with an 80 kV Transmission Electron Microscope (JEM1010, Japan).

Figure 22:
FIG. 22 is the result of confirming brain tumor targeting of gold nanoparticle complexes (Lf-AuNP) absorbed in a brain tumor animal model by a Bio-TEM (transmission electron microscope).
Figure 22:
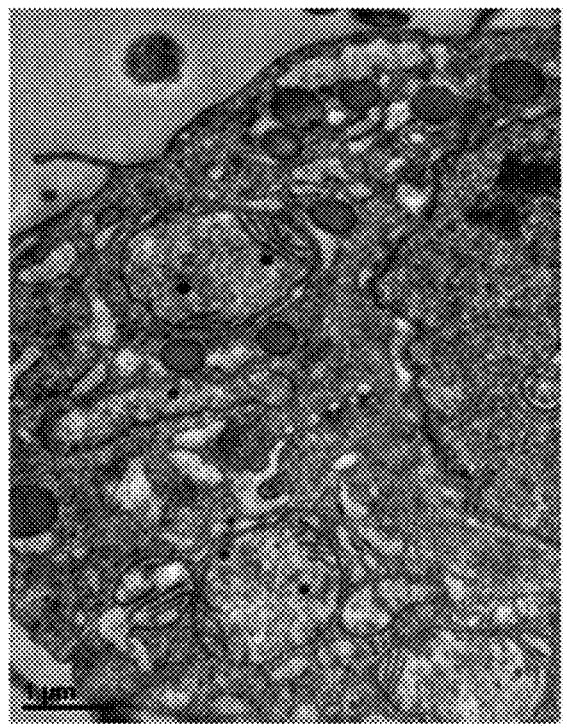

As shown in FIG. 22, a large amount of gold nanoparticle complex could be confirmed at the site where brain tumors were caused, and thus the brain tumor tissue targeting effect according to the present invention could be confirmed again.

Example 10: Identification of In Vivo Distribution Using Animal Model 10-1. Identification of In Vivo Distribution of Gold Nanoparticles Through ICP-MS This example was intended to confirm an in vivo distribution of the gold nanoparticle complex orally adsorbed, using an animal model. Specifically, the gold nanoparticle complex (200 μl) at a concentration of 60 mg/kg was orally absorbed via oral gavage, and then blood samples were collected 1, 6 and 24 hours after absorption through Retro-Orbital plexus bleeding techniques. Particularly, after 24 hours, the small intestine, liver, spleen and kidney were extracted together with the collection of blood, and the amount of gold nanoparticles present in the obtained blood and organs was measured through ICP-MS. On the other hand, as the control group, a group treated with general gold nanoparticles (AuNP) was used.

Figure 23:
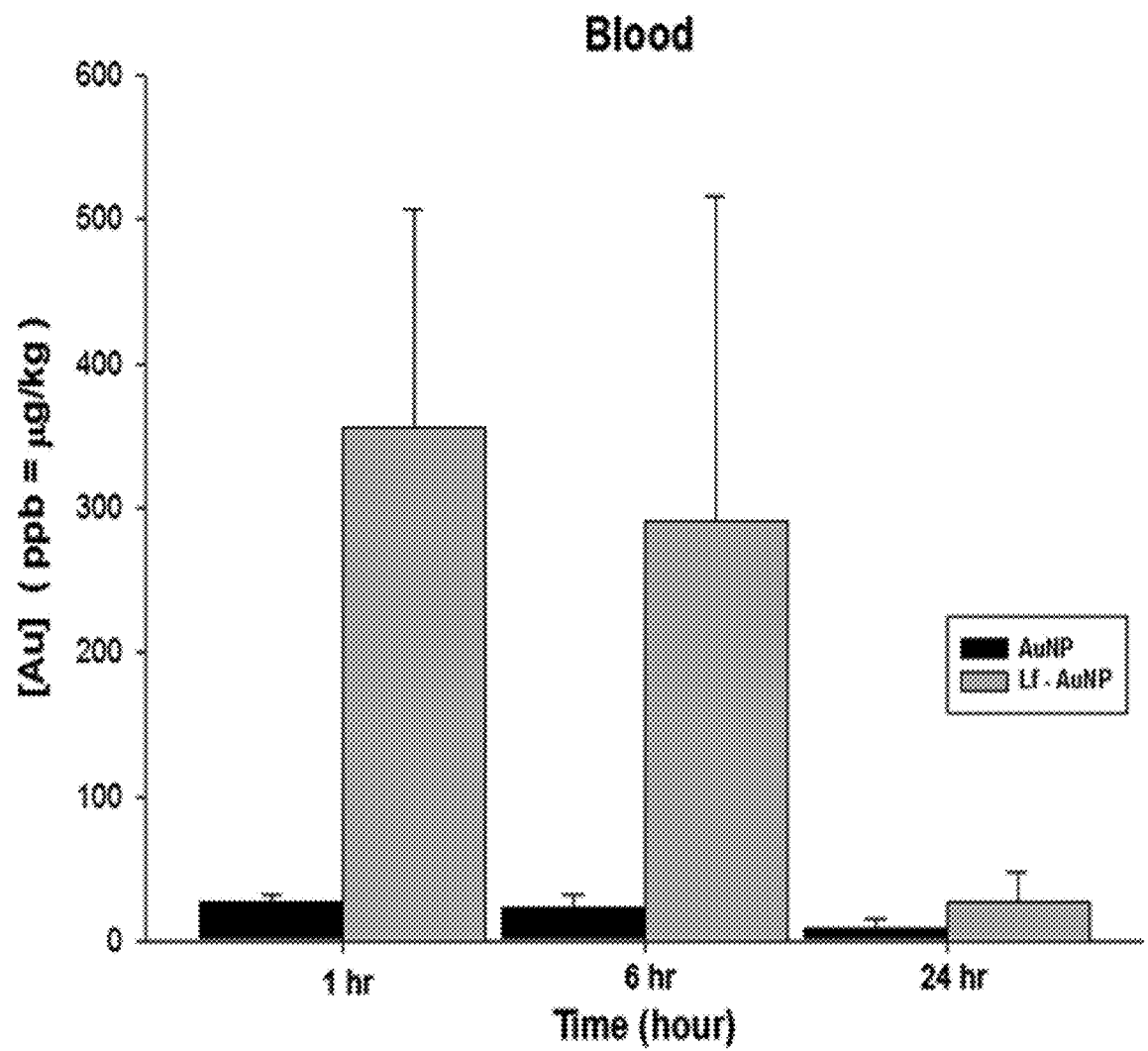
FIG. 23 is the result of comparing the amounts of gold nanoparticles present in the blood at intervals of 1, 6, and 24 hours after oral administration of gold nanoparticle complexes (Lf-AuNP) and gold nanoparticles (AuNP).

As a result, as shown in FIG. 23, in the case of blood, the amount of gold nanoparticles in the group treated with the gold nanoparticle complex at 1, 6 and 24 hours was significantly higher than that of the control group, and after 1 hour, the amount was measured 6 times or more, whereby it could be seen that the gold nanoparticle complex has an oral absorption rate higher than general gold nanoparticles.

Figure 24:
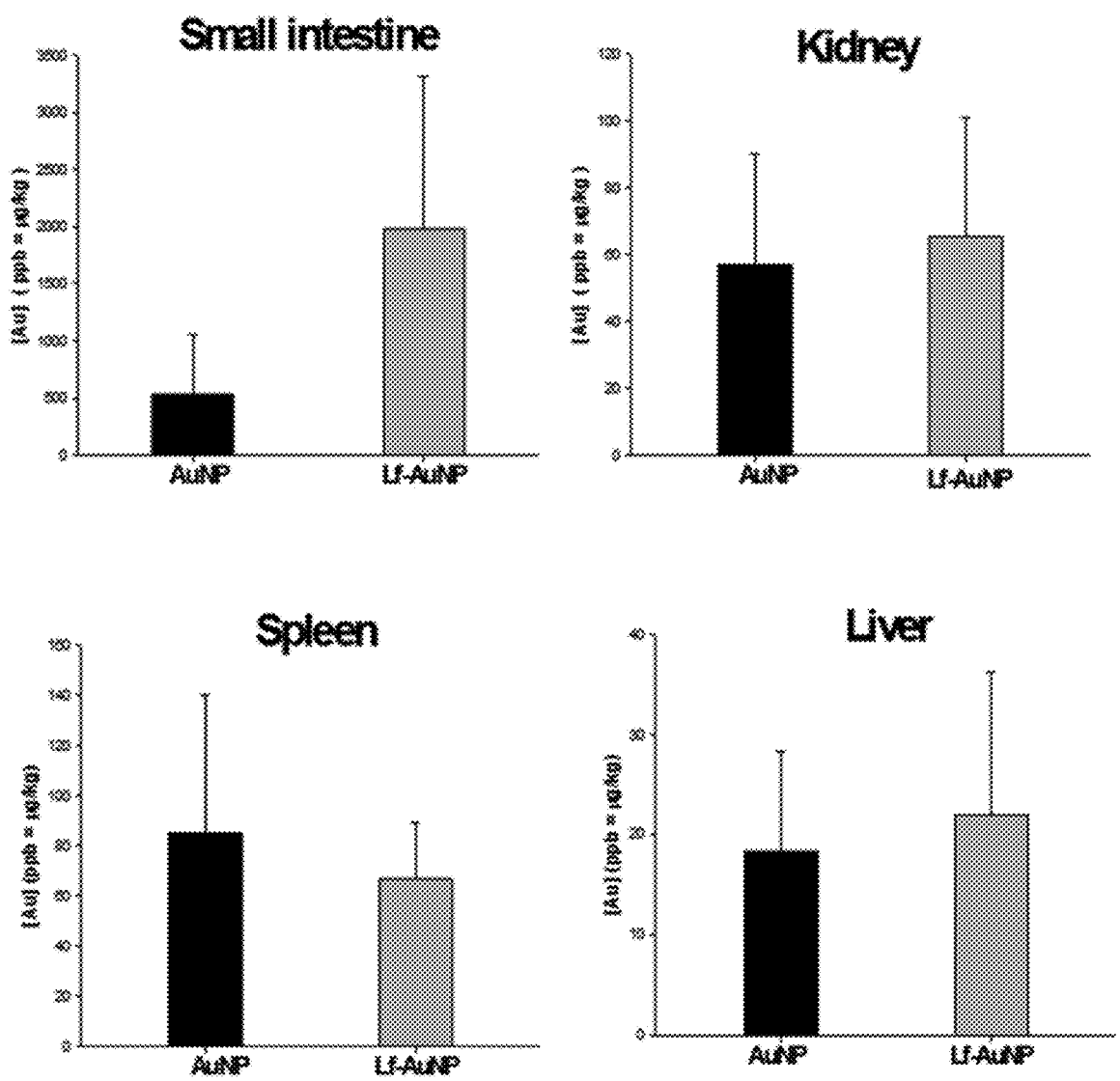
FIG. 24 is the result of comparing the amounts of gold nanoparticles present in kidney, small intestine, spleen, or liver tissues 24 hours after oral administration of gold nanoparticle complexes (Lf-AuNP) and gold nanoparticles (AuNP).

In addition, reviewing distribution by each organ, as shown in FIG. 24, in the case of the small intestine, the amount of gold nanoparticles was significantly increased in the group orally administered with the gold nanoparticle complex as compared with the group orally administered with gold nanoparticles, while in liver, spleen and kidney there was no significant difference from the group orally administered with gold nanoparticles.

10-2. Identification of In Vivo Distribution of Gold Nanoparticles Through Immunohistochemical Staining (IHC Staining) Using Lactoferrin Antibody This example was intended to confirm an in vivo distribution of the gold nanoparticle complex orally adsorbed using an animal model. Specifically, the gold nanoparticle complex (200 μl) at a concentration of 60 mg/kg was orally administered via oral gavage and after 24 hours, the kidney, liver, lung and spleen were extracted. For the obtained organs, the immunohistochemical staining using a lactoferrin antibody was performed, and gold nanoparticle complexes present in the organs were observed with a fluorescence microscope. On the other hand, as the control group, the untreated group (con) was used.

Figure 25A:
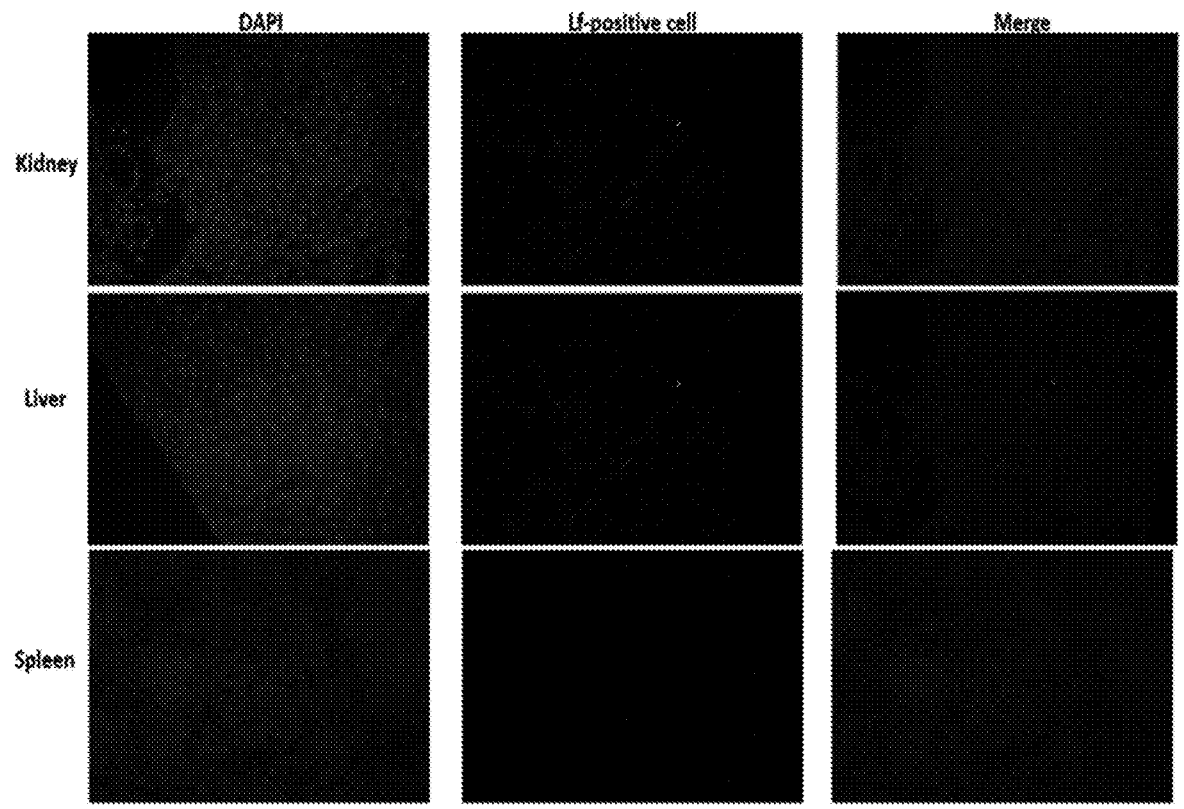
FIG. 25a is the result of confirming distribution in kidney, liver, or spleen tissues by immunohistochemical stain and a fluorescence microscope after oral administration of a phosphate buffered saline solution containing lactoferrin.
Figure 25B:
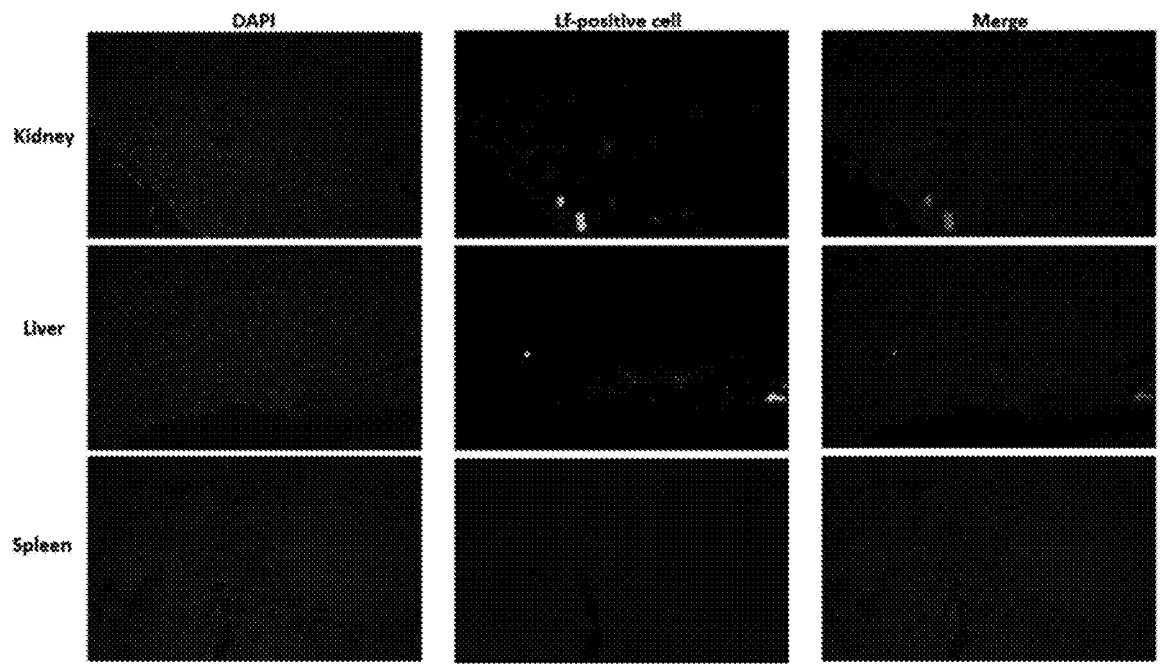
FIG. 25b is the result of confirming distribution in kidney, liver, or spleen tissues by immunohistochemical stain and a fluorescence microscope after oral administration of gold nanoparticle complexes (Lf-AuNP).

As a result, as shown in FIG. 25, the distribution of the gold nanoparticle complex by the organ was observed in accordance with the results of FIG. 24, and thus excellent oral absorption of the gold nanoparticle complex could be again confirmed.

Example 11: Evaluation of Toxicity Using Animal Model

In this example, the in vivo tissue toxicity of gold nanoparticle complex orally absorbed was confirmed in an animal model as a target. Specifically, the gold nanoparticle complex (200 μl) at a concentration of 60 mg/kg was orally administered 10 times at an interval of 2 days via oral gavage. After 20 days, the kidney, liver, lung and spleen were extracted, and after preparing their paraffin blocks, the prepared tissue slices were stained with H & E staining and observed. As the control group, the untreated group (con) was used.

Figure 26:
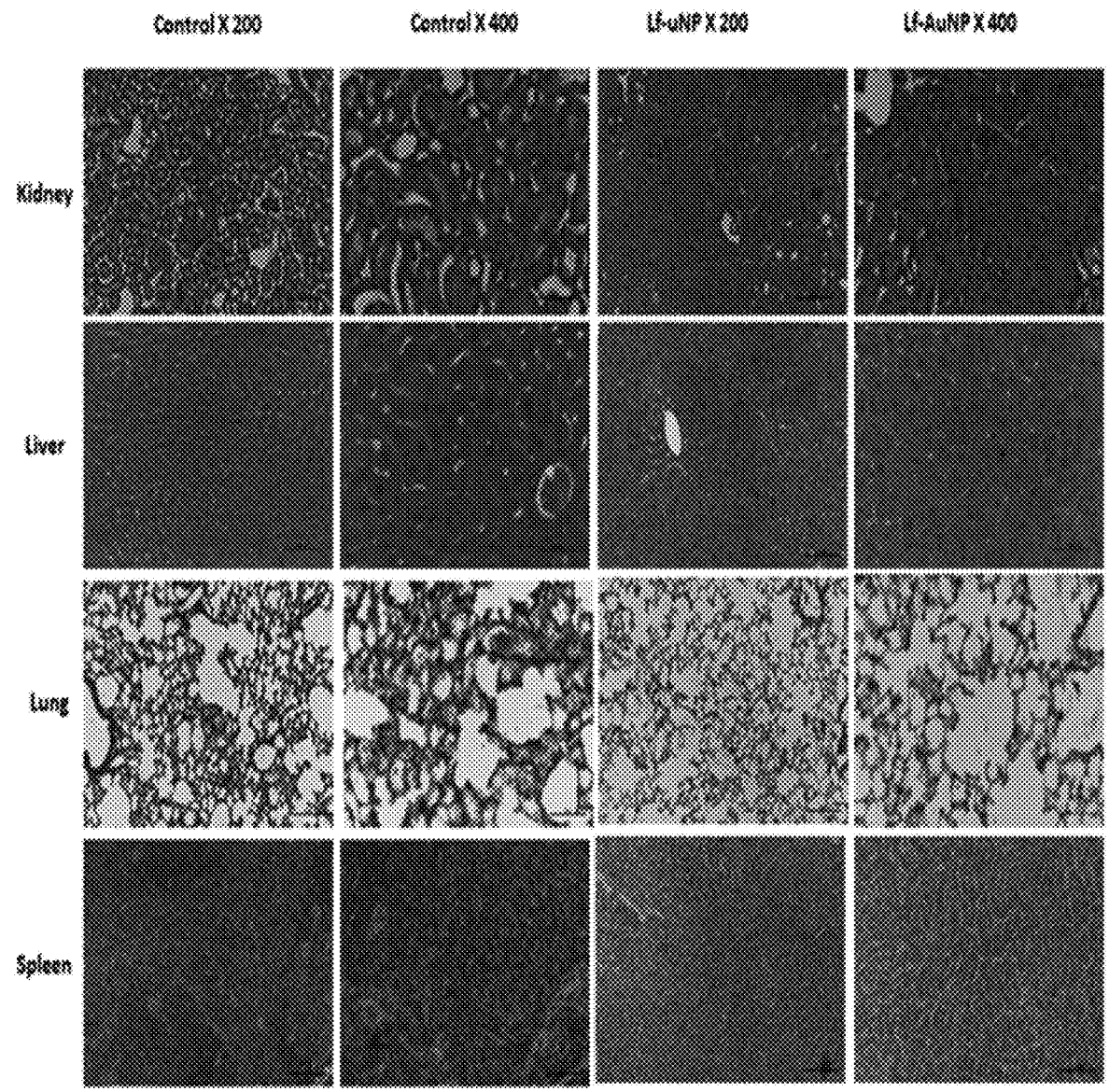
FIG. 26 is the result of confirming toxicity of gold nanoparticle complexes on kidney, liver, lung and spleen tissues in an animal model through H & E (Hematoxylin-eosin stain) stain and an optical microscopy.

As a result, as shown in FIG. 26, the group treated with the gold nanoparticle complex and the control group were no histological difference in the kidney, liver, lung, spleen and the like, whereby it could be seen that the gold nanoparticle complex according to the present invention showed no specific toxicity.

Example 12: Identification of Photothermal Effect on Brain Tumors Using Animal Model This example was intended to confirm the photothermal effect of the gold nanoparticle complex orally administered using a brain tumor animal model. Specifically, after the animal model was allowed to remain in its fasted state for 6 hours, the gold nanoparticle complex (200 µl) at a concentration of 60 mg/kg was orally administered. After 24 hours, a brain tumor lesion site and a left site of the body were irradiated with a laser having a wavelength of 532 nm under a condition of 4 w/cm$^2$ for 180 seconds using an LRS-0532 DPSS Laser System Laser Glow Part Number: R5310B1FL, and the change in temperatures was measured in real time using an FLIR C2 thermal imaging camera. As the comparative group, PBS (200 µl) and gold nanoparticles (200 µl) at a concentration of 11 mg/kg were orally administered via oral gavage.

Figure 27:
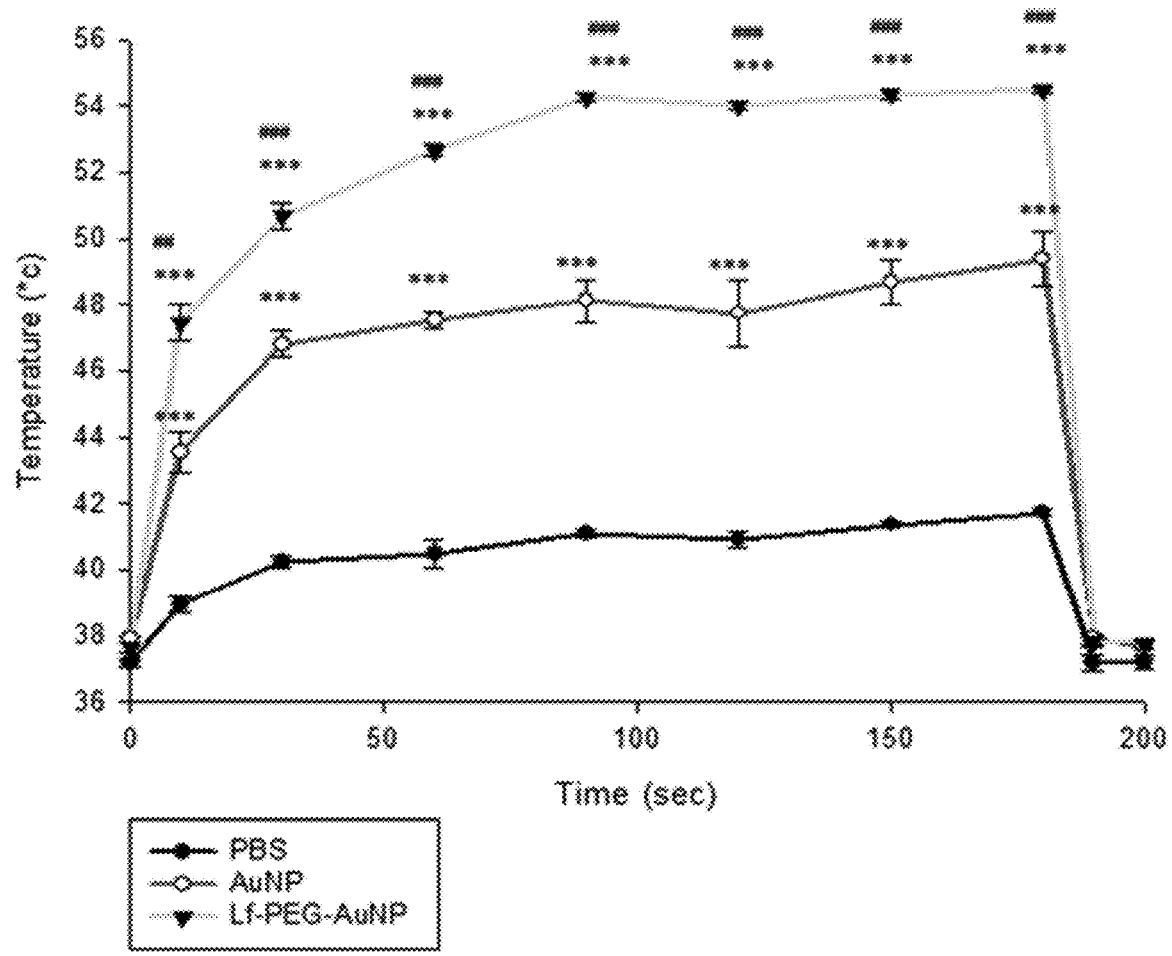
FIG. 27 is the result obtained by irradiating brain tumor tissues with a 532 nm laser for 3 minutes, 24 hours after oral administration of phosphate buffered saline (PBS), gold nanoparticles (AuNP), and gold nanoparticle complexes (Lf-AuNP) to brain tumor models, and then confirming the temperature change according to this.
Figure 28:
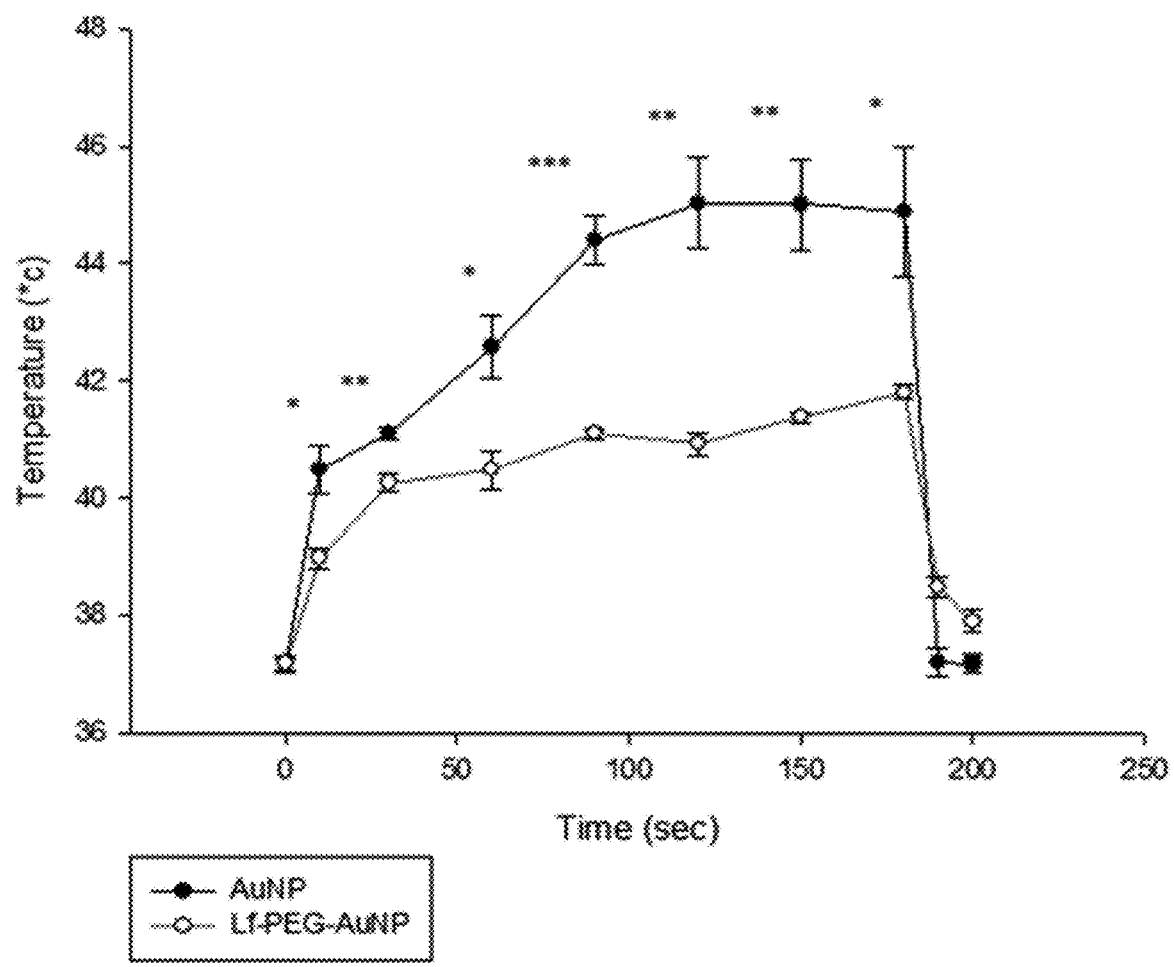
FIG. 28 is the result obtained by irradiating the body part, instead of the brain tumor tissues, with a 532 nm laser for 3 minutes, 24 hours after oral administration of phosphate buffered saline (PBS), gold nanoparticles (AuNP), and gold nanoparticle complexes (Lf-AuNP) to brain tumor models, and then confirming the temperature change according to this.

As a result, as shown in FIG. 27, by high brain tumor targeting of the gold nanoparticle complex and the distance maintaining effect (about 5 nm) between the gold nanoparticle complexes due to the repulsion effect of Lf-PEG, excellent photothermal effect by light of 532 wavelength bands could be observed. In addition, as shown in FIG. 28, it could be confirmed that the gold nanoparticle complex in the other body part had a photothermal effect reduced by 4.5° C., as compared to the gold nanoparticle, due to the high brain tumor targeting of the gold nanoparticle complex.

Example 13: Identification of Photothermal Therapeutic Effect of Orally Administered Gold Nanocomplex on Brain Tumors Using Animal Model This example was intended to confirm the photothermal effect due to brain tumor targeting of the gold nanoparticle complex orally administered using a brain tumor animal model. Specifically, after the animal model was allowed to remain in its fasted state for 6 hours, the gold nanoparticle complex (200 µl) at a concentration of 60 mg/kg was orally administered. After 24 hours, a process of irradiating a brain tumor lesion site and a left site of the body with a laser having a wavelength of 532 nm under a condition of 4 w/cm$^2$ for 180 seconds using an LRS-0532 DPSS Laser System Laser Glow Part Number: R5310B1FL, was therapeutically performed 5 times at an interval of 3 days, that is, for 15 days. As the comparative group, PBS (200 µl) and gold nanoparticles (200 µl) at a concentration of 11 mg/kg were orally administered via oral gavage.

Thereafter, the mouse was sacrificed, and then the brain was extracted. After fixing the obtained brain tissues in 4% paraformaldehyde for 2 days and then placing in a Leica TP1020 Semi-enclosed Benchtop Tissue Processor to complete processes of interstitial washing, dewatering, transparentizing and paraffin-penetrating, the tissues completing paraffin penetration were placed in a base mold to facilitate slicing, and hardened by dispensing paraffin. Then, tissue slices with a thickness of 20 µm were prepared using a paraffin rotation type slicer, Leica RM2145 Microtome. For the obtained slices, deparaffinizing, wetting and washing processes were further carried out.

13-1. Identification of Killing Effect of Brain Tumor Cells Through Tunel Assay

Figure 29:
FIG. 29 is the result obtained by photothermally treating a brain tumor animal model with gold nanoparticle complexes (Lf-AuNP) and then confirming the extracted brain tumor tissues by a Tunel assay and H & E stain.
Figure 29:
Figure 29:
Figure 29:
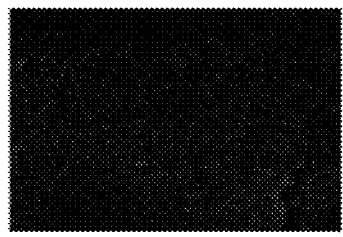
Figure 29:
Figure 29:
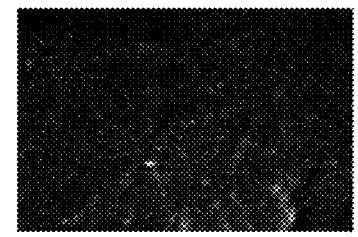

The obtained tissue slices were observed using a DeadEnd Fluorometric TUNEL System (Promega, USA) kit. The Tunel assay is an experiment using TdT (terminal deoxynucleotidyl transferase) enzymes and UTP (uridine triphosophate) DNA fragments, where cell necrosis or death in brain tumor tissues was confirmed through fragmentation of DNA. As a result, as shown in FIG. 29, a large number of fragmented DNA fragments were detected in the group (Lf-AuNP) photothermally treated using the gold nanoparticle complex as compared with the group (AuNP) using gold nanoparticles, so that the excellent brain tumor cell killing effect could be confirmed.

13-2. Identification of Volume Reduction Effect of Brain Tumor Tissues Through Nissl Staining The obtained tissue slices were stained with a mixed solution of a cresyl violet stock solution obtained by dissolving 0.2 g of cresyl violet-acetate in 150 ml of distilled water and a buffer solution obtained by mixing 0.1 M acetic acid and 0.1 M sodium acetate, and observed. As the control group, a group (Saline) using physiological saline was used, and as the comparative group, a group (Laferrin) orally administered with lactoferrin, a group (AuNP) orally administered with gold nanoparticles, a group (laser untreated: Lf-AuNP) orally administered with gold nanoparticle complex, and a group (AuNP) orally administered with gold nanoparticles and treated with laser were used.

Figure 30:
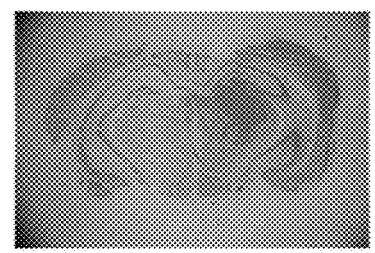
FIG. 30 is the result obtained by photothermally treating a brain tumor animal model with gold nanoparticle complexes (Lf-AuNP) and then confirming the extracted brain tumor tissues by Nissl stain.
Figure 30:
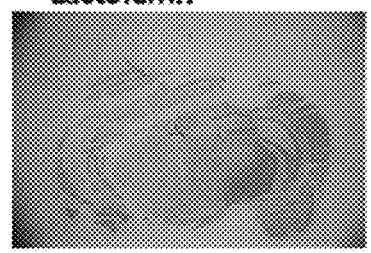
Figure 30:
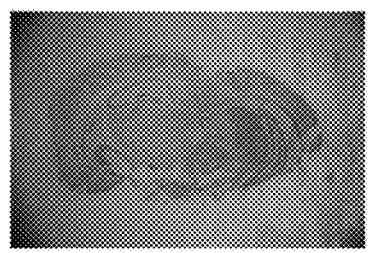
Figure 30:
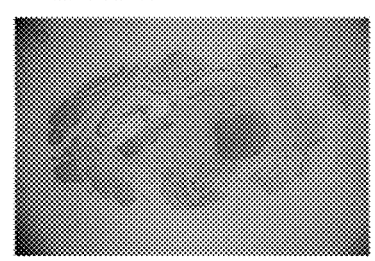
Figure 30:
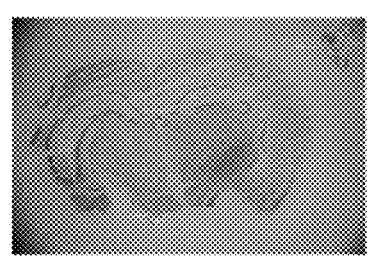
Figure 30:
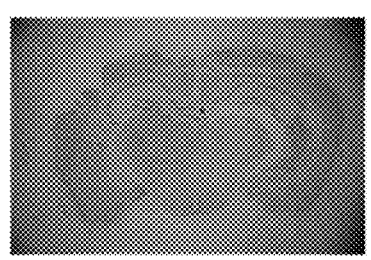
Figure 31:
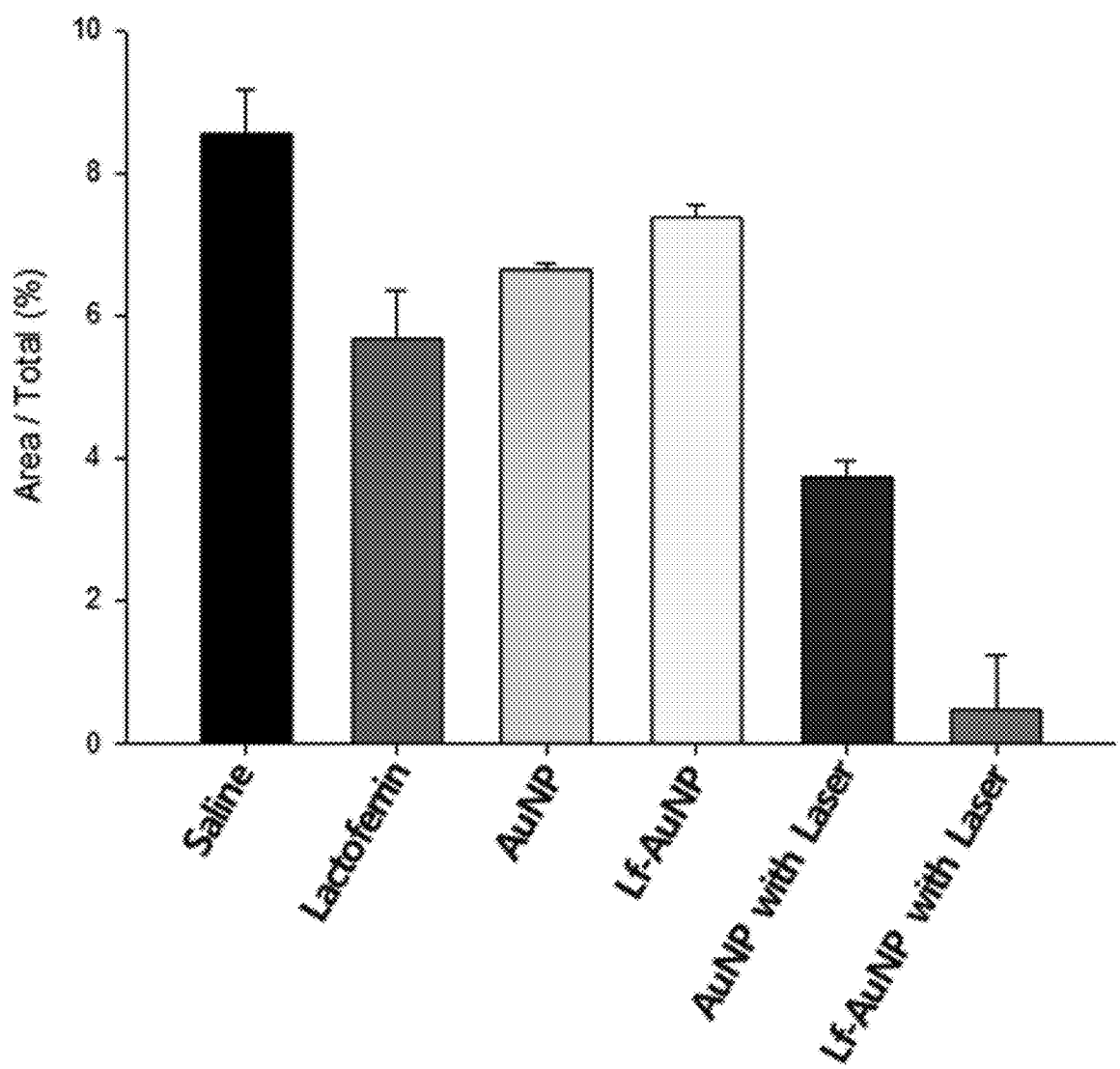
FIG. 31 is the result quantitatively showing Nissl staining results of the extracted brain tumor tissues after photothermally treating a brain tumor animal model with gold nanoparticle complexes (Lf-AuNP).

As a result, as shown in FIGS. 30 and 31, it could be confirmed that in the group (Lf-AuNP with laser) photothermally treated, using the gold nanoparticle complex, the volume of brain tumor tissues was significantly reduced as compared with other comparative groups, particularly, the group (AuNP with laser) photothermally treated, using gold nanoparticles.

Taken together with these results, the gold nanoparticle complex according to the present invention has improved oral absorption rates and brain targeting through lactoferrin bound to the surface of the complex and has enhanced biocompatibility and stability through glutathione bonded to another surface. In addition, the PEG bound to lactoferrin exhibited excellent photothermal therapeutic effect on brain tumors by improving stability of the lactoferrin in the gastrointestinal tract and the systemic circulation process, and lowering cohesion between nanoparticles through repulsion between PEGs. Based on such a fact, the gold nanoparticle complex according to the present invention can be usefully utilized as an orally administered composition for photothermal or photodynamic therapy targeting brain tumors.

It will be understood that the foregoing description of the present invention is for illustrative purposes and without changing the technical idea or essential features of the present invention, those skilled in the art can easily modify them into other specific forms. Therefore, it should be understood that the above-described examples are illustrative in all aspects and not restrictive.

The invention claimed is:

1. A nanoparticle complex consisting of gold nanoparticles that are covalently modified with glutathione and lactoferrin, and wherein said lactoferrin is further bound to polyethylene glycol.

2. The nanoparticle complex according to claim 1, wherein said glutathione is covalently linked to the gold nanoparticles by disulfide bonds.

3. The nanoparticle complex according to claim 1, wherein said nanoparticle complex has an average diameter from 4 nm to 20 nm as measured by transmission electron microscopy.

4. A pharmaceutical composition suitable for oral administration to a subject in need thereof and comprising the nanoparticle complex according to claim 1.

5. A pharmaceutical composition for a treatment of brain tumor in a subject in need thereof by a photothermal or photodynamic therapy and comprising the nanoparticle complex according to claim 1.

* * * * *